(12) United States Patent
Brukilacchio et al.

(10) Patent No.: US 8,279,442 B2
(45) Date of Patent: Oct. 2, 2012

(54) LIGHT EMITTING DIODE ILLUMINATION SYSTEM

(75) Inventors: Thomas J. Brukilacchio, Reading, MA (US); Arlie R. Conner, Portland, OR (US)

(73) Assignee: Lumencor, Inc., Beaverton, OR (US)

( * ) Notice: Subject to any disclaimer, the term of this patent is extended or adjusted under 35 U.S.C. 154(b) by 0 days.

(21) Appl. No.: 13/012,658

(22) Filed: Jan. 24, 2011

(65) Prior Publication Data

US 2011/0116261 A1    May 19, 2011

Related U.S. Application Data

(63) Continuation of application No. 12/187,356, filed on Aug. 6, 2008, now Pat. No. 7,898,665.

(60) Provisional application No. 60/954,140, filed on Aug. 6, 2007.

(51) Int. Cl.
    *G01N 21/25* (2006.01)
(52) U.S. Cl. ......................... 356/417; 356/420
(58) Field of Classification Search .......... 362/227–228, 362/216–225, 217.01–217.17, 253–254, 362/260, 307–310, 257, 296.01, 317, 326–329, 362/23–30; 356/402–420, 432, 43–50
See application file for complete search history.

(56) References Cited

U.S. PATENT DOCUMENTS

| | | | |
|---|---|---|---|
| 1,998,054 A | 4/1935 | McBurney | |
| 3,313,337 A | 4/1967 | Bernat | |
| 3,637,285 A | 1/1972 | Stewart | |
| 3,759,604 A | 9/1973 | Thelen | |
| 3,881,800 A | 5/1975 | Friesem | |
| 3,982,151 A | 9/1976 | Ludovici | |
| 4,003,080 A | 1/1977 | Maiman | |
| 4,298,820 A | 11/1981 | Bongers | |
| 4,371,897 A | 2/1983 | Kramer | |
| 4,510,555 A | 4/1985 | Mori | |
| 4,539,687 A | 9/1985 | Gordon | |
| 4,626,068 A | 12/1986 | Caldwell | |
| 4,642,695 A | 2/1987 | Iwasaki | |
| 4,644,141 A | 2/1987 | Hagen | |
| 4,695,332 A | 9/1987 | Gordon | |
| 4,695,732 A | 9/1987 | Ward | |

(Continued)

FOREIGN PATENT DOCUMENTS

CA    2 280 398    4/2000

(Continued)

OTHER PUBLICATIONS

International Search Report dated Dec. 31, 2008, Application No. PCT/US2008/072394, 10 pages.

(Continued)

*Primary Examiner* — Tri T Ton
(74) *Attorney, Agent, or Firm* — Fliesler Meyer LLP

(57) ABSTRACT

In various embodiments of the invention, a unique construction for Light Emitting Diodes (LEDs) with at least one luminescent rod and extracting optical elements is used to generate a variety of high brightness light sources with different emission spectra. In an embodiment of the invention, forced air cooling is used to cool the luminescent rod. In an embodiment of the invention, totally internal reflected light can be redirected outward and refocused. In another embodiment of the invention, light emitted by the luminescent rod is out-coupled for use in a variety of applications. In various embodiments of the invention, a plurality of independent narrow band colors can be coaxially combined.

31 Claims, 14 Drawing Sheets

U.S. PATENT DOCUMENTS

| | | | |
|---|---|---|---|
| 4,695,762 A | 9/1987 | Berkstresser | |
| 4,713,577 A | 12/1987 | Gualtieri | |
| 4,724,356 A | 2/1988 | Daehler | |
| 4,798,994 A | 1/1989 | Rijpers | |
| 4,804,850 A | 2/1989 | Norrish et al. | |
| 4,852,985 A | 8/1989 | Fujihara et al. | |
| 4,937,661 A | 6/1990 | Van Der Voort | |
| 4,995,043 A | 2/1991 | Kuwata | |
| 5,052,016 A | 9/1991 | Mahbobzadeh | |
| 5,089,860 A | 2/1992 | Deppe | |
| 5,109,463 A | 4/1992 | Lee | |
| 5,126,626 A | 6/1992 | Iwasaki | |
| 5,128,846 A * | 7/1992 | Mills et al. | 362/224 |
| 5,137,598 A | 8/1992 | Thomas | |
| 5,193,015 A | 3/1993 | Shanks | |
| 5,200,861 A | 4/1993 | Moskovich | |
| 5,226,053 A | 7/1993 | Cho | |
| 5,231,533 A | 7/1993 | Gonokami | |
| 5,233,372 A | 8/1993 | Matsumoto | |
| 5,249,195 A | 9/1993 | Feldman | |
| 5,285,131 A | 2/1994 | Muller | |
| 5,289,018 A | 2/1994 | Okuda | |
| 5,312,535 A | 5/1994 | Waska | |
| 5,315,128 A | 5/1994 | Hunt | |
| 5,332,892 A | 7/1994 | Li et al. | |
| 5,345,333 A | 9/1994 | Greenberg | |
| 5,363,398 A | 11/1994 | Glass | |
| 5,416,342 A | 5/1995 | Edmond et al. | |
| 5,416,617 A | 5/1995 | Loiseaux | |
| 5,418,584 A | 5/1995 | Larson | |
| 5,428,476 A | 6/1995 | Jensen | |
| 5,469,018 A | 11/1995 | Jacobsen | |
| 5,475,281 A | 12/1995 | Heijboer | |
| 5,478,658 A | 12/1995 | Dodabalapur | |
| 5,489,771 A | 2/1996 | Beach et al. | |
| 5,493,177 A | 2/1996 | Muller | |
| 5,500,569 A | 3/1996 | Blomberg | |
| 5,542,016 A | 7/1996 | Kaschke | |
| 5,616,986 A | 4/1997 | Jacobsen | |
| 5,644,676 A | 7/1997 | Blomberg | |
| 5,658,976 A | 8/1997 | Carpenter | |
| 5,669,692 A | 9/1997 | Thorgersen | |
| 5,671,050 A | 9/1997 | De Groot | |
| 5,674,698 A | 10/1997 | Zarling | |
| 5,690,417 A | 11/1997 | Polidor et al. | |
| 5,715,083 A | 2/1998 | Takayama | |
| 5,719,391 A | 2/1998 | Kain | |
| 5,757,014 A | 5/1998 | Bruno | |
| 5,781,338 A | 7/1998 | Kapitza et al. | |
| 5,803,579 A | 9/1998 | Turnbull et al. | |
| 5,804,919 A | 9/1998 | Jacobsen | |
| 5,808,759 A | 9/1998 | Okamori et al. | |
| 5,827,438 A | 10/1998 | Blomberg | |
| 5,833,827 A | 11/1998 | Anazawa | |
| 5,858,562 A | 1/1999 | Utsugi | |
| 5,864,426 A | 1/1999 | Songer | |
| 5,942,319 A | 8/1999 | Oyama | |
| 5,955,839 A | 9/1999 | Jaffe | |
| 5,984,861 A | 11/1999 | Crowley | |
| 6,110,106 A | 8/2000 | MacKinnon et al. | |
| 6,154,282 A | 11/2000 | Lilge et al. | |
| 6,198,211 B1 | 3/2001 | Jaffe | |
| 6,204,971 B1 | 3/2001 | Morris | |
| 6,222,673 B1 | 4/2001 | Austin | |
| 6,293,911 B1 | 9/2001 | Imaizumi et al. | |
| 6,299,338 B1 | 10/2001 | Levinson | |
| 6,304,584 B1 | 10/2001 | Krupke | |
| 6,366,383 B1 | 4/2002 | Roeder | |
| 6,392,341 B2 | 5/2002 | Jacobsen | |
| 6,404,127 B2 | 6/2002 | Jacobsen | |
| 6,404,495 B1 | 6/2002 | Melman | |
| 6,422,994 B1 | 7/2002 | Kaneko et al. | |
| 6,444,476 B1 | 9/2002 | Morgan | |
| 6,513,962 B1 | 2/2003 | Mayshack et al. | |
| 6,517,213 B1 | 2/2003 | Fujita et al. | |
| 6,529,322 B1 | 3/2003 | Jones | |
| 6,542,231 B1 | 4/2003 | Garrett | |
| 6,544,734 B1 | 4/2003 | Briscoe | |
| 6,594,075 B1 | 7/2003 | Kanao et al. | |
| 6,608,332 B2 | 8/2003 | Shimizu | |
| 6,614,161 B1 | 9/2003 | Jacobsen et al. | |
| 6,614,179 B1 | 9/2003 | Shimizu et al. | |
| 6,637,905 B1 | 10/2003 | Ng | |
| 6,642,652 B2 | 11/2003 | Collins | |
| 6,649,432 B1 | 11/2003 | Eilers | |
| 6,674,575 B1 | 1/2004 | Tandler et al. | |
| 6,680,569 B2 | 1/2004 | Mueller-Mach et al. | |
| 6,685,341 B2 | 2/2004 | Ouderkirk et al. | |
| 6,690,467 B1 | 2/2004 | Reel | |
| 6,717,353 B1 | 4/2004 | Mueller | |
| 6,747,710 B2 | 6/2004 | Hall | |
| 6,791,259 B1 | 9/2004 | Stokes et al. | |
| 6,791,629 B2 | 9/2004 | Moskovich | |
| 6,795,239 B2 | 9/2004 | Tandler et al. | |
| 6,843,590 B2 | 1/2005 | Jones | |
| 6,869,206 B2 | 3/2005 | Zimmerman et al. | |
| 6,870,165 B2 | 3/2005 | Amirkhanian | |
| 6,926,848 B2 | 8/2005 | Le Mercier | |
| 6,958,245 B2 | 10/2005 | Seul et al. | |
| 6,960,872 B2 | 11/2005 | Beeson et al. | |
| 6,981,970 B2 | 1/2006 | Karni | |
| 6,991,358 B2 | 1/2006 | Kokogawa | |
| 6,995,355 B2 | 2/2006 | Rains, Jr. et al. | |
| 7,009,211 B2 | 3/2006 | Eilers | |
| 7,011,421 B2 | 3/2006 | Hulse et al. | |
| 7,035,017 B2 | 4/2006 | Tadic-Galeb | |
| 7,083,610 B1 | 8/2006 | Murray et al. | |
| 7,153,015 B2 | 12/2006 | Brukilacchio | |
| 7,192,161 B1 | 3/2007 | Cleaver et al. | |
| 7,205,048 B2 | 4/2007 | Naasani | |
| 7,208,007 B2 | 4/2007 | Nightingale et al. | |
| 7,211,833 B2 | 5/2007 | Slater, Jr. et al. | |
| 7,239,449 B2 | 7/2007 | Leitel et al. | |
| 7,300,175 B2 | 11/2007 | Brukilacchio | |
| 7,316,497 B2 | 1/2008 | Rutherford et al. | |
| 7,384,797 B1 | 6/2008 | Blair | |
| 7,416,313 B2 | 8/2008 | Westphal et al. | |
| 7,422,356 B2 | 9/2008 | Hama et al. | |
| 7,427,146 B2 | 9/2008 | Conner | |
| 7,445,340 B2 | 11/2008 | Conner | |
| 7,467,885 B2 | 12/2008 | Grotsch et al. | |
| 7,488,088 B2 | 2/2009 | Brukilacchio | |
| 7,488,101 B2 | 2/2009 | Brukilacchio | |
| 7,498,734 B2 | 3/2009 | Suehiro et al. | |
| 7,540,616 B2 | 6/2009 | Conner | |
| 7,633,093 B2 | 12/2009 | Blonder et al. | |
| 7,637,627 B2 * | 12/2009 | Moffat et al. | 362/234 |
| 7,709,811 B2 | 5/2010 | Conner | |
| 7,746,560 B2 | 6/2010 | Yamazaki | |
| 7,832,878 B2 | 11/2010 | Brukilacchio | |
| 7,837,348 B2 | 11/2010 | Narendran et al. | |
| 7,854,514 B2 | 12/2010 | Conner | |
| 7,857,457 B2 | 12/2010 | Rutherford et al. | |
| 8,029,142 B2 | 10/2011 | Conner | |
| 2001/0055208 A1 | 12/2001 | Kimura | |
| 2002/0109844 A1 | 8/2002 | Christel et al. | |
| 2002/0127224 A1 | 9/2002 | Chen | |
| 2003/0044160 A1 | 3/2003 | Jones et al. | |
| 2003/0095401 A1 | 5/2003 | Hanson et al. | |
| 2003/0230728 A1 | 12/2003 | Dai | |
| 2003/0233138 A1 | 12/2003 | Spooner | |
| 2004/0090600 A1 | 5/2004 | Blei | |
| 2004/0247861 A1 | 12/2004 | Naasani | |
| 2005/0062404 A1 | 3/2005 | Jones et al. | |
| 2005/0116635 A1 | 6/2005 | Walson et al. | |
| 2005/0146652 A1 | 7/2005 | Yokoyama et al. | |
| 2005/0152029 A1 | 7/2005 | Endo | |
| 2005/0184651 A1 | 8/2005 | Cheng | |
| 2005/0201899 A1 | 9/2005 | Weisbuch | |
| 2005/0260676 A1 | 11/2005 | Chandler | |
| 2005/0263679 A1 | 12/2005 | Fan et al. | |
| 2006/0002131 A1 | 1/2006 | Schultz et al. | |
| 2006/0030026 A1 | 2/2006 | Garcia | |
| 2006/0060872 A1 | 3/2006 | Edmond et al. | |
| 2006/0060879 A1 | 3/2006 | Edmond | |
| 2006/0114960 A1 | 6/2006 | Snee | |
| 2006/0170931 A1 | 8/2006 | Guo | |

| | | | |
|---|---|---|---|
| 2006/0237658 | A1 | 10/2006 | Waluszko |
| 2006/0282137 | A1 | 12/2006 | Nightingale et al. |
| 2007/0053184 | A1 | 3/2007 | Brukilacchio |
| 2007/0053200 | A1 | 3/2007 | Brukilacchio |
| 2007/0058389 | A1 | 3/2007 | Brukilacchio |
| 2007/0064202 | A1 | 3/2007 | Moffat et al. |
| 2007/0086006 | A1 | 4/2007 | Ebersole et al. |
| 2007/0126017 | A1 | 6/2007 | Krames et al. |
| 2007/0211460 | A1 | 9/2007 | Ravkin |
| 2007/0253733 | A1 | 11/2007 | Fey |
| 2007/0279914 | A1 | 12/2007 | Rutherford et al. |
| 2007/0279915 | A1 | 12/2007 | Rutherford et al. |
| 2007/0280622 | A1 | 12/2007 | Rutherford et al. |
| 2007/0281322 | A1 | 12/2007 | Jaffe et al. |
| 2007/0284513 | A1 | 12/2007 | Fan |
| 2007/0297049 | A1 | 12/2007 | Schadwinkel et al. |
| 2008/0079910 | A1 | 4/2008 | Rutherford et al. |
| 2008/0291446 | A1 | 11/2008 | Smith |
| 2009/0122533 | A1 | 5/2009 | Brukilacchio |
| 2009/0196046 | A1 | 8/2009 | Rutherford et al. |
| 2009/0268461 | A1 | 10/2009 | Deak et al. |
| 2010/0188017 | A1 | 7/2010 | Brukilacchio |

FOREIGN PATENT DOCUMENTS

| | | |
|---|---|---|
| EP | 1 426 807 | 12/2003 |
| GB | 0943756 | 12/1963 |
| GB | 2 000 173 A | 1/1979 |
| JP | 02-804873 | 7/1998 |
| JP | 2005-195485 | 7/2005 |
| JP | 2005-243973 | 9/2005 |
| JP | 2006-049814 | 2/2006 |
| JP | 2007-133435 | 5/2007 |
| KR | 10-2006-0055934 | 5/2006 |
| KR | 10-2006-0089104 | 8/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report for PCT/US2010021843 dated Aug. 19, 2010, 9 pages.
Extended European Search Report for PCT/US2008072394 dated Oct. 7, 2011, 9 pages.
Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).
Vlasenko, N.A., et al., "Interference of Luminescent Emission from an Evaporated Phosphor," Opt. Spect., vol. 11, pp. 216-219 (1961).
Vlasenko, N.A., et al., "Investigation of Interference Effects in Thin Electroluminescent ZnS-Mn Films," Opt. Spect., vol. 28, pp. 68-71 (1970).
Poelman, D., et al., "Spectral Shifts in Thin Film Electroluminescent Devices: An Interference Effect," J. Phys. D: Appl. Phys., vol. 25, pp. 1010-1013 (1992).
Tuenge, R.T., "Current Status of Color TFEL Phosphors," Electroluminescence—Proceedings of the Sixth International Workshop on Electroluminescence, El Paso, Tex., pp. 173-177, May 1992.
Plasma Display Manufacturers of the American Display Consortium, "Recommended Research Topics on Plasma Display for the DARPA Sponsored Phosphor Center of Excellence," pp. 1-2, Mar. 24, 1993.
Yamamoto, Y., et al., "Optical Processes in Microcavities," Physics Today, pp. 66-73, Jun. 1993.
E.F. Schubert, E.F., et al., "Giant Enhancement of Luminescence Intensity in Er-doped $Si/SiO_2$ Resonant Cavities," Appl. Phys. Lett. vol. 61, No. 12, pp. 1381-1383, Sep. 21, 1992.
Yokoyama, H., "Physics and Device Applications of Optical Microcavities," Science, vol. 256, pp. 66-70, Apr. 3, 1992.
Haroche, S., et al., "Cavity Quantum Electrodynamics," Scientific American, pp. 54-62, Apr. 1993.
Depp, S.W., et al., "Flat Panel Displays," Scientific American, pp. 90-97, Mar. 1993.
Huo, D.T.C., et al., "Reticulated Single-Crystal Luminescent Screen," J. Electrochem. Soc., vol. 133, No. 7, pp. 1492-1497, Jul. 1986.
Hinds, E.A., "Spectroscopy of Atoms in a Micron-Sized Cavity," (date and periodical title unknown), pp. 18-19.
Whitaker, Jerry C., "Electronic Displays: Technology, Design, and Applications," McGraw-Hill, Inc., pp. 185-192 (1994).
Hecht, Jeff, "Diverse fiberoptic systems require varied sources," Laser Focus World, vol. 36, No. 1, pp. 155-161, Jan. 2000.
Hamberg, I. and Granqvist, C.G., "Evaporated Sn-doped $In_2O_3$ films: Basic optical properties and applications to energy-efficient windows," Journal of Applied Physics, vol. 60, No. 11, pp. R123-R159, Dec. 1, 1986.
World Watch, Photonics Spectra, "IR Reflective Coating Boosts Bulb's Output, Recycling of IR Energy Saves Power, Cuts Costs" pp. 40-41, Jan. 1991.
Jenmar Visual Systems, Sunnyvale, CA, 4 pages, no date, but at least as early as Oct. 15, 1998.
DDS™ Rear Projection Screens, LORS™ Reflection Screens, ©1998 Physical Optics Corporation, Torrance, CA, 2 pages.
Schott Glass Technologies, Inc., Schott Total Customer Care, Contrast Enhancement Filters, Duryea, PA, 6 pages, Jan. 1998.
Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.
Young, L., "Multilayer Interference Filters with Narrow Stop Bands," Applied Optics, vol. 6, No. 2, pp. 297-312, Feb. 1967.
Hemingway, D.J. and Lissberger, P.H., "Effective Refractive Indices of Metal-Dielectric Interference Filters," Applied Optics, vol. 6, No. 3, pp. 471-476, Mar. 1967.
Holloway, R.J. And Lissberger, P.H., "The Design and Preparation of Induced Transmission Filters," Applied Optics, vol. 8, No. 3, pp. 653-660, Mar. 1969.
Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.
Lissberger, P.H., "Coatings with Induced Transmission," Applied Optics, vol. 20, No. 1, pp. 95-103, Jan. 1, 1981.
Pelletier, E. and MacLeod, H.A., "Interference Filters with Multiple Peaks," Journal of the Optical Society of America, vol. 72, No. 6, pp. 683-687, Jun. 1982.
Da-Lite Screen Company, Inc., www.da-lite.com, 46 pages website downloads as of Oct. 8, 1998.
Stewart Filmscreen Corporation®, www.stewartfilm.com, 34 pages website downloads as of Oct. 8, 1998.
Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).
Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.
Deck, L., et al., "Two color light-emitting-diode source for high precision phase-shifting interferometry", Optics Letters, vol. 18, No. 22, Nov. 15, 1993, pp. 1899-1901.
Morgan, C. G., et al., << New Approaches to Lifetime-Resolved Luminescence Imaging, Journal of Fluorescence, vol. 7, No. 1, 1997, pp. 65-73.
International Search Report dated Jun. 19, 2012 for Application No. PCT/US2011/063030, 11 pages.

* cited by examiner

LIGHT EMITTING DIODE ILLUMINATION SYSTEM

PRIORITY CLAIM

This application is a continuation of U.S. patent application Ser. No. 12/187,356, entitled: "LIGHT EMITTING DIODE ILLUMINATION SYSTEM", inventor: Thomas J. Brukilacchio, filed Aug. 6, 2008; which claims priority to U.S. Provisional Patent Application Ser. No. 60/954,140, entitled: "LIGHT EMITTING DIODE ILLUMINATION SYSTEM", inventor: Thomas J. Brukilacchio, filed Aug. 6, 2007; each of which applications are incorporated herein by reference in their entirety.

CROSS REFERENCE TO RELATED APPLICATIONS

This application is related to the following application, which was filed on Aug. 5, 2008 herewith:

"LIGHT EMITTING DIODE ILLUMINATION SYSTEM" by Thomas J. Brukilacchio, application Ser. No. 12/186,475, Attorney Docket No. LUMEN-01019US0 SRM/AGC which application is incorporated herein by reference in its entirety.

FIELD OF THE INVENTION

This invention, in general, relates to high brightness illumination sources and more particularly to the use of Light Emitting Diodes (LEDs) as a source of illumination.

BACKGROUND OF THE INVENTION

There is a significant need for high brightness broad band illumination sources to provide optical fiber coupled illumination for surgical endoscopy and other applications where extremely high brightness sources are needed such as in projection systems and high speed industrial inspection. Prior art typically utilize short arc lamps such as high pressure mercury, metal halide, and xenon. These lamps are capable of very high luminous emittance and are therefore suitable sources for the etendue limited fiber optic coupled illumination systems. Approximately 85% of the high brightness illumination sources in use in the operating room today are based on compact short arc xenon lamps. The problems associated with these lamp technologies, however, include poor luminous efficacy thereby requiring high power and associated means of cooling, short lifetime, high voltage operation (typically kilovolts required to turn them on), high cost, and use of mercury which is becoming an environmental hazard and is in the process of undergoing regulations in numerous countries throughout the world.

Only recently has there been recognition that Light Emitting Diodes (LEDs) may provide sufficient illumination to be used to replace more traditional light sources in endoscopic illumination systems. In particular, LEDs provide much improved lifetime, lower cost of ownership, lower power consumption (enabling some battery operated portable devices), decreased cooling requirements, and freedom form mercury relative to conventional arc lamps. Additionally they can be readily modulated which can be a significant advantage in many applications. To date no LED based endoscopic illumination system commercially exists that equals or exceeds the luminous intensity of the compact xenon arc lamp systems. The invention described herein has the potential of meeting and exceeding the output of the best arc lamps systems available today

BRIEF DESCRIPTION OF THE DRAWINGS

This invention is described with respect to specific embodiments thereof. Additional features can be appreciated from the Figures in which.

DETAILED DESCRIPTION OF THE INVENTION

Figure 1:
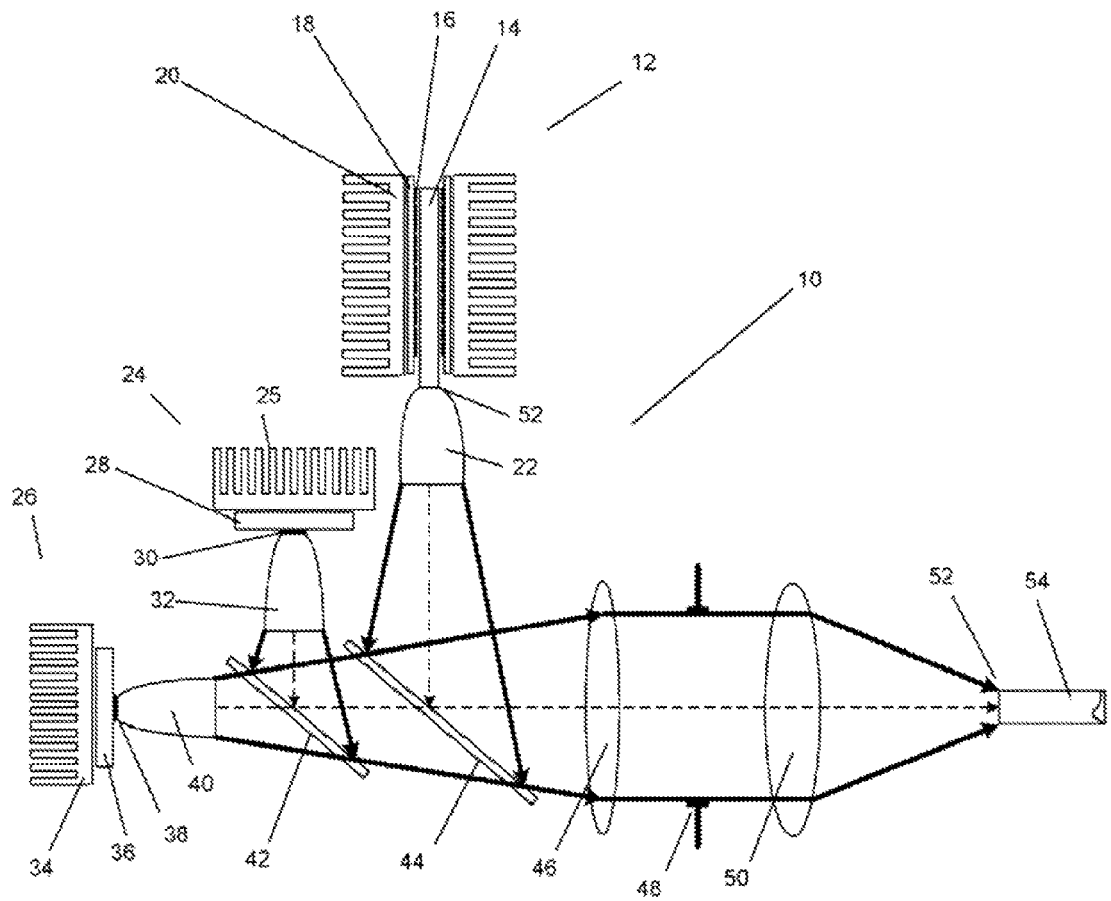
FIG. 1 shows an embodiment of the light emitting diode illumination system, where three spectral coupled sources are combined to provide a high brightness light source.

Prior to LED based systems conventional arc lamp based projection systems were used comprised of a short arc lamp typically of the high pressure mercury, metal halide, or xenon lamp variety. The primary disadvantage of the short arc technology is lamp life, which is typically in the 500 to 1000 hour range. The cost of the arc lamp itself and the service cost to replace the lamps over the life of the product can be many multiples of the original cost of the complete illumination system. The arc lamp needs time to stabilize, so tends to be left on for hours, even when the actual usage time is minutes, so that 500 hours can be accrued in a few months of usage. Additional benefits of the LED technology include reduced power consumption, low voltage operation, light intensity stability, no warm-up period is required, ability to control correlated color temperature (CCT) and color rendering index (CRI), and the ability to modulate the source. The ability to modulate the source can be a significant benefit. For example, most of the endoscopic systems in use today are coupled to a video camera. Typically video cameras incorporate an electronic shutter and typically the video signal is not integrated continuously. Thus, there is an opportunity to modulate the LED source in synchronization with the shutter. During the time when the shutter is closed, the LED light source does not need to be on. Thus, for example, if the shutter was open 50% of the time, the light source can be modulated in synchronization producing 50% less heat. Thus, for the same average input power to the LED light source the light output can be increased by an amount dependant on the operating point of the LED source with respect to efficiency.

A more conventional approach to producing white light by LEDs is to deposit a phosphor powder, typically of Ce:YAG (cerium doped yttrium aluminum garnet, $Y_3Al_5O_{12}:Ce^{3+}$) suspended in an encapsulant material such as silicone, onto a blue LED die or die array with a peak wavelength between about 445 nm and 475 nm. The light absorbed by the phosphor is converted to yellow light, which combines with the scattered blue light to produce a spectrum that appears white. The apparent color temperature is a function of the density and thickness of the phosphor suspended in the encapsulant. While this approach is efficient, the amount of white light produced per unit area per unit solid angle is fundamentally limited by the amount of blue light extracted from the blue LED die or die array, the quantum efficiency of the phosphor, the phosphors thermal quenching, and the back scattering, which is a function of the particle size of the phosphor or other luminescent material. While it is feasible to place a solid phosphor such as single crystal Ce:YAG over the top of the blue LED die or die array, the efficiency of such a device would be limited by the total internal reflection of such a luminescent material due to its high index of refraction and more importantly, the reduction due to Stokes and quantum efficiencies, scattering and back-emission reduce the quantity of light and and this is contradictory to the goal of producing high brightness.

In various embodiments of the invention, a white light or multi-color illumination system incorporates a luminescent rod material which is excited along its length by a linear array of LEDs. In an embodiment of the present invention, the luminescent material is a single crystal. In an alternative embodiment of the invention, the luminescent material is a sintered ceramic Ce:YAG (cerium doped yttrium aluminum gamete, $Y_3Al_5O_{12}:Ce^{3+}$) and the LEDs are blue GaN based surface emitting devices. In an embodiment of the invention, the green and/or yellow output spectrum from the rod can be coupled to a collection optic which converts the light emitted from the aperture of the rod to a larger dimension with a smaller solid angle. In an embodiment of the invention, the light emitted can be imaged to a fiber bundle or other light transporting medium such as a liquid light guide (LLG). In an embodiment of the invention, the output of the luminescent rod and collection optic can be combined with the output of other directly coupled LED arrays in the blue and red spectral regions to produce white light. In an embodiment of the invention, the outputs of two or more luminescent rod subsystems may be combined to produce desired spectra of nearly unlimited shape. In an embodiment of the invention at least four non-overlapping narrow color bands can be combined into a single coaxial light bundle. In an embodiment of the invention a six color illumination system can be obtained, by adding at least one laser diode to at least one luminescent rod subsystem and combining with other solid state light sources. In an embodiment of the invention all of the independent and non-overlapping spectral bands are produced by using LEDs and laser diodes, in concert with at least one luminescent rod to enhance the brightness of the delivered light and all such channels are capable of electronic intensity control, electronic shuttering and can be modulated at rates exceeding 10 KHz.

Blue and red LED modules can be produced to equal or exceed the brightness of conventional high brightness light sources such as compact xenon arc lamps. However, the efficiency of LEDs in the true green spectrum, especially in the spectral region of 555 nm are of comparatively low efficiency and are not sufficiently bright compared to arc lamps. Typically light generated from LEDs in the spectral region of 555 nm is achieved by applying a thin layer of directly over LED die emitting blue light. The light from the phosphor particles is partially absorbed and partially scattered. A combination of the scattered blue light and the absorbed light re-emitted as luminescent light at longer wavelengths typically in the green and red spectral regions, produces white light. It is possible to increase the thickness of the phosphor layer to fully extinguish the blue LED excitation energy but the total amount of green and/or red light produced by the phosphor, is reduced due to the increased back-scattering of the thicker phosphor layer and thus a green LED made of a blue LED with a green phosphor is far less efficient than a direct bandgap green (e.g. InGaN) LED. In particular there are high efficiency laser diodes at wavelengths above approximately 620 nm and below approximately 410 nm. For the green and yellow regions, there are a wide variety of diode-pumped solid state (DPSS), frequency doubled YAG lasers but these light sources have numerous problems of manufacture, temperature-control requirements and are expensive. Furthermore, it is not always desirable to have single-wavelength coherent light for bio-analytical work. Thus, a luminescent rod with a broad emission band output spectral shape (20 to 150 nm) can be extremely useful for exciting a range of fluorophores covalently attached to analyte molecules.

The amount of white light produced can be increased by increasing the current density to the LED up to the point where the output of the LED rolls over and no longer increases with increasing current. The brightness of any LED made by in this general configuration is fundamentally limited by the internal and external quantum efficiency of the LED die, the quantum efficiency of the luminescent material, the amount of scattering by the particles, the thermal quenching properties of the die, and the die junction temperature.

In contrast, the present invention is not limited by the current density of the LED as the length of the rod material can be increased to increase the number of excitation LED die and thereby increasing the luminescence output. For example, a high performance LED die with a 1 mm square area coated with a high performance phosphor can produce approximately 200 Lumens with a heat sink temperature near room temperature at the maximum current density (i.e., before rolling over and no longer producing more light with further increases in current density). Even with extraordinary cooling measures the phosphor-on-LED approach can yield at best green/yellow light densities of 500 mW per square millimeter at best with the current state of the art blue InGaN LEDs. By contrast, with the present invention we have demonstrated greater than 5 watts emitted from the same size surface using a luminescent rod material.

In an embodiment of the invention, a luminescent rod with a 1 mm square cross sectional area and a length of 50 mm can have approximately 100 LEDs exciting the luminescent rod. In an embodiment of the invention, a conservative efficiency of 30% can result in an output of more than an order of magnitude higher photometric power with each LED operating at current densities significantly lower than the maximum current density. Furthermore, if higher output was required the length of the rod can be increased along with an increase in the number of LEDs exciting the luminescent rod. Thus in various embodiments of the present invention, a means of producing output in the green portion of the spectrum results in higher brightness than can be achieved by even the best xenon short arc lamps.

The present invention relates to high brightness illumination systems. In particular, the present invention represents an LED based light source for improved illumination systems relative to arc lamp and other LED based light source systems. In an embodiment of the invention, the illumination system 10 of FIG. 1 is comprised of one or more LED die or die array modules 12, 24 and 26 spectrally and spatially combined by means such as dichroic beam splitters 42 and 44 coupled to a common source aperture 52 which substantially conserves the etendue or area, solid angle, index squared product. In an embodiment of the invention, a luminescence rod system couples into an optical fiber bundle to provide the high luminous power and high brightness required for bio-analytical and medical endoscopic applications. Other high brightness applications include, but are not limited to, projection systems, industrial illumination, photo curing, spot lights, and medical photodynamic therapy.

In FIG. 1 the LED source module 12 is comprised of a central rod 14 of luminescent material such as single crystal or sintered ceramic Ce:YAG, and other luminescent materials including $(Lu_{1-x-y-a-b}Y_xGd_y)_3(Al_{1-z-c}Ga_zSi_c)_5O_{12-c}N:Ce_aPr_b$ with $0<x<I$, $0<y<1$, $0<z</=0.1$, $0<a<=0.2$, $0<b<=0.1$, and $0<c<1$ for example $Lu_3Al_5O_{12}:Ce^{3+}$, $Y_3Al_5O_{12}:Ce^{3+}$ and $Y_3Al_{4.8}Si_{0.2}O_{11.8}N_{0.2}:Ce^{3+}$ emitting yellow-green light; and $(Sr_{1-x-y}Ba_xCa_y)_{2-z}Si_{5-a}Al_aN_{8-a}O_a:Eu_z^{2+}$ where $0<=a<5$, $0<x<=1$, $0<=y<=1$, and $0<z<=1$ for example $Sr_2Si_5N_8:Eu^{3+}$, emitting red light. Other candidates include $(Sr_{1-a-b}Ca_bBa_c)Si_xN_yO_z:Eu_a^{2+}$ where $a=0.002$ to $0.20$, $b=0.0$ to $0.25$, $c=0.0$ to $0.25$, $x=1.5$ to $2.5$, $y=1.5$ to $2.5$, and $z=1.5$ to $2.5$ for example $SrSi_2N_2O_2:Eu^{2+}$; $(Sr_{1-u-v-x}Mg_uCa_vBa_x)(Ga_{2-y-z}Al_zIn_zS_4):Eu^{2+}$ for example $SrGa_2S_4:Eu^{2+}$; $(Sr_{1-x-y}Ba_xCa_y)_2SiO_4:Eu^{2+}$ for example $SrBaSiO_4:Eu^{2+}$; $(Ca_{1-x}Sr_x)S:Eu^{2+}$ where $0<x<=1$ for example $CaS:Eu^{2+}$ and $SrS:Eu^{2+}$; $(Ca_{1-x-y-z}Sr_xBa_yMg_z)_{1-x}(Al_{1a+b}B)Si_{1-b}N_{3-b}O_b:RE_n$ where $0<=x<=1$, $0<=y<=1$, $0<=z<=1$, $0<=a<=1$, $0<=b<=1$ and $0.002<=n<=0.2$ and RE is either europium(II) or cerium (III) for example $CaAlSiN_3:Eu^{2+}$ or $CaAl_{1.04}Si_{0.96}N_3:Ce^{3+}$; and $M_xv+Si_{12-(m+n)}Al_{m+n}O_nN_{16-n}$, with $x=m/v$ and M comprised of a metal preferably selected from the group comprising Li, M, Ca, Y, Sc, Ce, Pr, Nf, Sm, Eu, Gd, Tb, Dy, Ho, Er, Tm, Yb, Lu or mixtures including for example $Ca_{0.75}Si_{8.625}Al_{3.375}N_{0.625}:EU_{0.25}$ as disclosed in U.S. patent application Ser. No. 11/290,299 to Michael R. Krames and Peter J. Schmidt (publication #2007/0126017) which is herein explicitly incorporated by reference in its entirety; and nano-phosphors embedded in a suitable matrix such as high index plastic or glass, with LED die positioned along its length in a linear array of die or a single long LED die attached to a high thermal conductivity board 18, such as copper or aluminum core printed circuit board, which in turn is attached to heat sink 20. In an embodiment of the invention, the luminescent rod 14 can have the properties of high absorption of light in one part of the spectrum, blue in the case of Ce:YAG, emission with high quantum yield in a wavelength region generally longer than the excitation wavelength band, high index of refraction to trap a significant portion of the luminescent light produced such that it is guided or transmitted down the length of the rod toward an emitting aperture 52. In an embodiment of the invention, the emitting aperture can be index matched to an optical concentrator 22 such as a compound parabolic concentrator (CPC), compound elliptical concentrator (CEC), compound hyperbolic concentrator (CHC), taper, or faceted optic. The concentrators can be index matched and made of solid dielectric. In an alternative embodiment of the invention, the concentrators can be index matched and made of a liquid dielectric. The purpose of the concentrator is two-fold. First, it would be made of a material with an index of refraction approaching that of the rod (approximately 1.82 for Ce:YAG). Second, it would act to convert the light emitted over a hemisphere (2 steradians) to an area and solid angle that can be readily imaged through dichroic beam splitters and re-imaging optics while substantially preserving the etendue (area, solid angle, index squared product) thereby maximizing the brightness. In another alternative embodiment of the invention, a lens can be used rather than an optical concentrator. A ball lens is especially useful as it can reduce the angular extent of the light source, allowing for simpler optical collection into or onto the desired target area. In many cases the optical index matching need not be perfect. In an embodiment of the invention, a suitable commercially available low index material (n~1.46) coupling gel can be applied between the luminescent rod and the half ball lens with resulting 80 to 90% extraction efficiency. With YAG:Ce as the luminescent material and a half ball lens of somewhat higher index, e.g. Schott type SF6 glass or S-LAH79 from Ohara, as much light as is trapped by the TIR light-guiding mechanism can be extracted, i.e. all the light that is guided within about a 57 degree half angle within the YAG medium.

In an embodiment of the invention, the output spectrum of the Ce:YAG rod source can cover the range between about 500 nm and 700 nm, with the predominant contribution in the green spectrum centered around 555 nm. In an embodiment of the invention, the combination of the light from a luminescent rod with that from a blue LED module 24 can produce white light suitable for many applications. For bioanalytical and medical illumination applications, however, the relative spectral content is typically required to result in a high color rendering index (CRI) on the order of 85 or greater. To accomplish this it is necessary to add additional light in the red spectral region from a third LED source module 26. In FIG. 1 dichroic beam splitter 42 can transmit the red light of LED module 26 and reflect the blue light of LED module 24. Dichroic beam splitter 44 can transmit the combined blue and red spectrum of combined LED modules 26 and 24 and reflect the green or yellow light of LED module 12. The combined white light spectrum from LED modules 12, 24, and 26 can then be imaged by lens elements 46 and 50 to fill the input aperture 52 of fiber optic light bundle 54. The lens elements 46 and 50 can be comprised of multiple lens elements which can include glasses or plastics of different dispersions to help optimize image quality. The lens systems aperture stops 48 can assure that the extent of the far field of the light from each LED module was similar so as not to result in color fringe effects at the edge of the illumination field. In particular in a microscope illuminator, when the Kohler method is utilized, each colored component should have the same far field distribution as the pupil of the illuminator is being imaged onto the biological specimen. The size of each LED source and its collection optics can be sized such as to produce substantially similar near and far field distributions for each LED module. The lens system can also include diffractive or reflective components to help reduce the number of or optical elements and to reduce overall package size. The relative position of the LED modules 12, 24, and 26 can be interchanged assuming that the dichroic beam splitters were changed in spectral characteristics to accommodate different arrangements. For example, LED modules 12 and 24 can be switched in position such that beam splitter 42 can transmit red light, reflect blue and green light and beam splitter 44 can transmit red and green and reflect blue light. The spectrum of the LED modules in a different system can include ultraviolet through mid infrared light assuming the optical elements were made of the proper transmitting materials and anti-reflection or reflection coatings. In an embodiment of the invention, the LED modules 24 and 26 can be comprised of a LED array index matched to the collection optic depending on the extraction efficiency and brightness of the LED die. The collection optics can be comprised of similar optics as detailed for the LED module 12, the optical concentrator, or alternative optics can be designed for index matching. In an alternative embodiment of the invention, the LED modules 24 and 26 can be comprised of a LED array not index matched to the collection optic again depending on the extraction efficiency and brightness of the LED die. The collection optics can be comprised of similar optics as detailed for the LED module 12, the optical concentrator, or alternative optics can be designed for no index matching. For example blue die from CREE (EZ1100) includes a micro lens array such that the benefit from index matching does not compensate for the increase in the etendue due to the index squared effect. Thus for the case of these high performance blue color dies, higher brightness is achieved by not index matching. In contrast, the red dies that are currently commercially available do not typically include microstructures on their surface to significantly enhance extraction efficiency and thus do benefit from encapsulation, not from a brightness standpoint, but from an efficiency standpoint which due to decreased thermal load translates into improved performance. For the above discussion, white light can consist of a combination of discrete wavelengths and/or discrete color bands and/or a continuous mix of such wavelengths spanning the ultra-violet visible infrared spectrum.

In various embodiments of the invention, heat sinks 12, 25, and 34 of FIG. 1 can be made out of any high thermal conductivity material including but not limited to copper and aluminum. The LED or LED arrays 16, 30, and 38 can be attached to LED printed circuit boards (PCBs) 18, 28, and 36 which can in turn be thermally and mechanically attached to heat sinks 12, 25, and 34 respectively. In various embodiments of the invention, the PCBs can be made out of a high thermal conductivity material including but not limited to copper, diamond, aluminum, or composite materials. In various embodiments of the invention, the thermal resistance between the back side of the LED die or die arrays can be minimized by direct eutectic attachment, soldering, or a thin layer of thermally conductive epoxy such as Diemat 6050. The high thermal conductivity PCBs can act as heat spreaders thereby reducing the heat flux density into the heat sinks 12, 25, and 34. The heat sinks can be cooled by direct convection with air, conduction with various coolant fluids such as water, or radiation into the surrounding environment. Heat pipes of various constructions have also been found to work very effectively as heat spreaders. Heat pipes and diamond can also be used as the PCB material as they both are very effective heat spreaders with performance well above that of pure copper.

Figure 2:
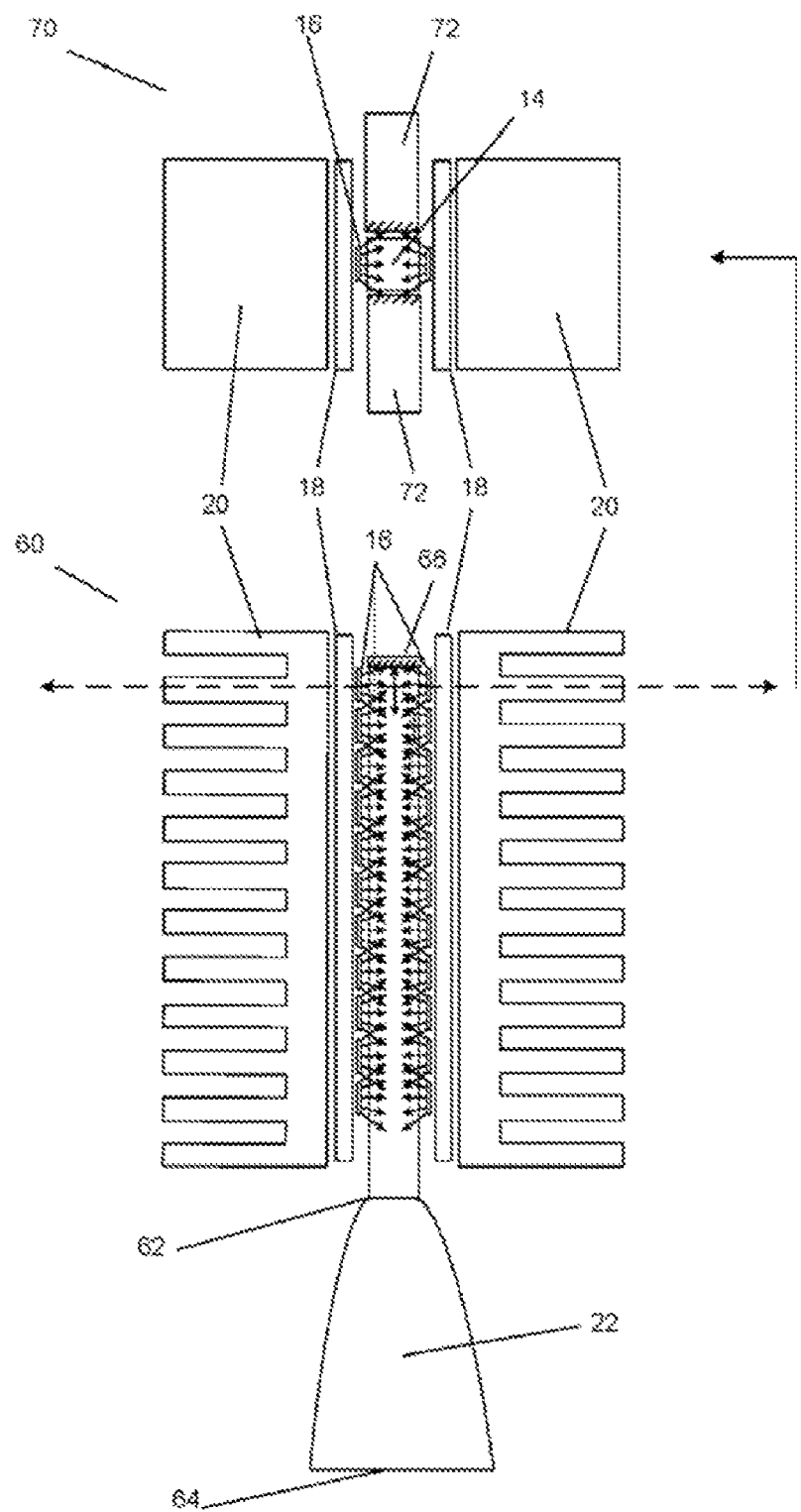
FIG. 2 is a detail of the solid rod luminescense material optical system comprised of the luminescent rod, LED excitation sources, heat sinks, and index matched output optic. The top view represents a cross sectional view.

FIG. 2 shows a detailed view 60 of the LED module 12 of FIG. 1 from the side and in cross section as indicated in 70. In an embodiment of the invention, the luminescent rod 14, can be a single crystal. In an alternative embodiment of the invention, the luminescent rod 14, can be a transparent sintered polycrystalline Ce:YAG. In various embodiments of the invention, the luminescent rod 14 can be characterized by high absorption in a spectral region such as blue in the region of 460 nm and very low extinction for wavelengths greater than the excitation wavelength band above 500 nm to 510 nm. The rod material 14 can also be characterized by exhibiting luminescence of the absorbed excitation light with high quantum yield. In an embodiment of the invention, the LED array 16 can be comprised of a blue LED die such as those manufactured by CREE Inc. called EZ1000, which are dimensionally on the order of 1 mm square by 0.120 mm thick. The light from the LED array can be transmitted through the outer wall of luminescent rod 14. The absorption coefficient of the luminescent rod 14 can be chosen to be fairly high, i.e. it can be doped to a level resulting in substantially all of the blue light being absorbed within the dimension of the rod prior to exiting the rod through its other side. To the extent that the excitation light was not absorbed with the first pass through the rod 14, mirrors 72 can be positioned with a reflective surface close to the rod so as to cause the excitation light to pass back into the rod one or more times to maximize absorption by the rod. The reflectivity of the LED die is on the order of 80%, which can also act to couple light that was not absorbed on the first pass through the rod back into it for another opportunity to be absorbed. The light can take multiple passes to be substantially absorbed. Given the finite reflectivity of the mirrors 72 and diffuse reflectivity of the LED die 16 it can be best to chose an extinction that can result in the order of 80% or more of the excitation light being absorbed on the first pass through the rod 14. It is also useful to place the LED surfaces as close to the rod as may be practical, while still allowing some air flow between these elements. In an embodiment of the invention, the LED surface is approximately 200 microns from the rod to ensure high excitation efficiency. In an alternative embodiment of the invention, the LED surface is approximately 120 to 320 microns from the rod. In this situation, a reasonable mechanical alignment tolerance corresponds to ±20 microns. In an alternative embodiment of the invention, the sides of the rod through which the excitation light is not passing initially can be coated with a high reflectivity coating. In this embodiment, the reflectivity can be very close to 100% so as not to lose substantial luminous power upon multiple reflections as the luminescent light is transmitted toward the output aperture 62. In another alternative embodiment of the invention, the outside surface of the rod can be not coated at all so as to allow a substantial portion of the light generated within the rod to be guided by total internal reflection (TIR) up the rod toward output aperture 62. In this embodiment, the fact that the luminescent material 14 has a relatively high index of refraction is fortunate as the higher the index of refraction greater percentage of the light that is generated within the rod will be guided by TIR toward the output aperture 62.

The luminescent light generated within the rod 14 would be substantially isotropic and thus would travel equally in all directions. Thus half of the light that is bound to the rod by TIR would travel in a direction opposite to the output aperture 62 toward mirror 66 which can act to send the light emitted in that direction back toward output aperture 62, thereby substantially doubling the light reaching output aperture 62. The mirror can also be effectively coated directly onto the end face of rod 14 in the vicinity of mirror 66.

Figure 3:
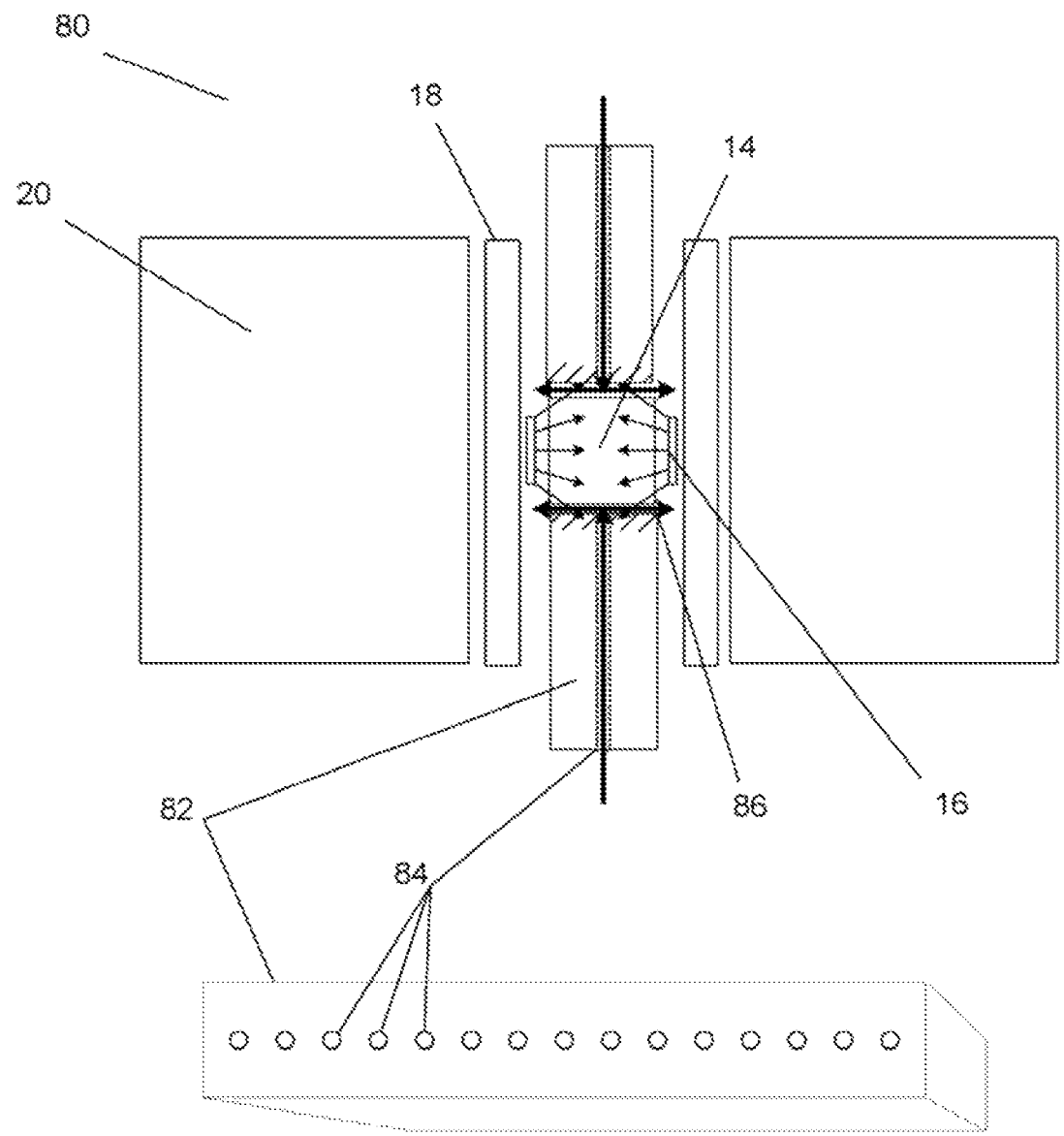
FIG. 3 shows an embodiment of the invention with the combined mirror and cooling system.

FIG. 3 shows an alternative embodiment 80 of the mirror elements 66 of FIG. 2 comprised of modified mirror elements 82 containing the addition of small holes 84 through which high pressure air can cool rod 14 by high pressure air impingement. The holes can be sufficiently small as to minimally affect the mirrored surface area of mirrors 82. High pressure air impingement has several times the film coefficient and thus heat transfer as compared to standard convected low pressure air. The effect of the slight increase in the index of refraction of the medium surrounding rod 14 on TIR can be minimal. If a direct contact cooling fluid was used without the sides of the rod being reflective, the higher than air index of refraction of the fluid can result in more loss out through the sides due to the decreased TIR internal angle, thereby reducing overall LED module efficiency. The reason it can be important to provide a means of removing heat build up from the rod is that there can be a small but finite heat absorption, convection and conduction to the rod from the LED array 16 that can cause an increase in temperature of the rod if there were no means of removing this heat. This heat rise can result in reduced overall performance due to thermal quenching of the luminescent rod material. Increasing the temperature of the rod material can decrease the quantum efficiency.

Figure 4:
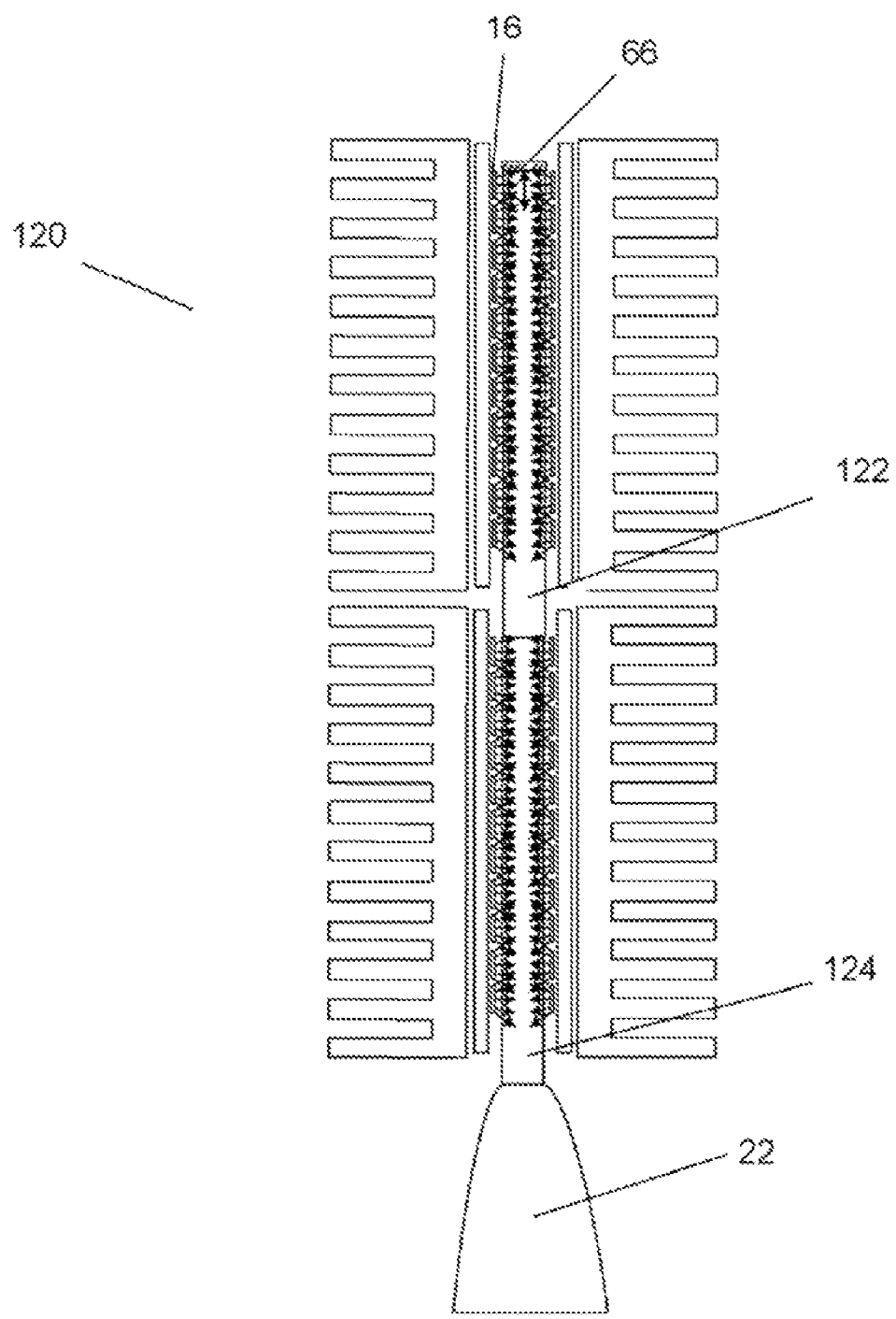
FIG. 4 shows an alternative embodiment of the invention containing two luminescent rod sources in series.

FIG. 4 shows an alternative embodiment 120 of LED module 12 of FIG. 1 where two modules 12 have been positioned in sequence to form a single multi-spectrum source. For example rod 122 of 120 can be made of a luminescent material with properties similar to those described for rod 14 for which the excitation band is within the long wavelength ultraviolet spectrum in the region of 240 nm to 420 nm. The high transmission region of the material can be in wavelengths longer than 420 nm and its luminescence can be in the blue to blue-green spectral region. Likewise rod 124 can have similar absorption properties but comprise luminescence in the green to red region of the spectrum. Both rods 122 and 124 can be characterized by high transmission in the spectral region containing wavelengths longer that 420 nm.

In an embodiment of the invention, the mirror 66 can act to reflect any light transmitted in the direction opposite output coupler 22 back toward 22. In this way, LED light module 120 can contain the full and desired spectrum of the white light source and can require neither supplemental LED modules 24 and 26 of FIG. 1 nor dichroic beam splitters 42 and 44. In an embodiment of the invention, an index matching material between the two rods 122 and 124 such as melted Schott SF6 glass or other suitable index matching material can be used. In an alternative embodiment of the invention, a single material or ceramic such as YAG (yttrium aluminum garnet) can use different dopants in the regions corresponding to rods 122 and 124 such that the rod is continuous and there is no need for an index matching medium. In another alternative embodiment of the invention, more than one dopant can be used evenly over the entire length of a single rod assuming the dopants did not interfere and reduce quantum efficiency. The length of the rods and excitation LED arrays can be increased to achieve higher flux out of collection optic 22. In various embodiments of the invention, an advantage of this technology over thin planar luminescent material coated on a LED, is that the output can be increased by increasing the length of the rod rather than increasing the power density of the excitation source thereby resulting in output flux many multiples of that which can be achieved by prior art. In an alternative embodiment of the invention, the output of the system of FIG. 4 can be directly coupled to an optical fiber bundle without the need for re-imaging optics.

Figure 5:
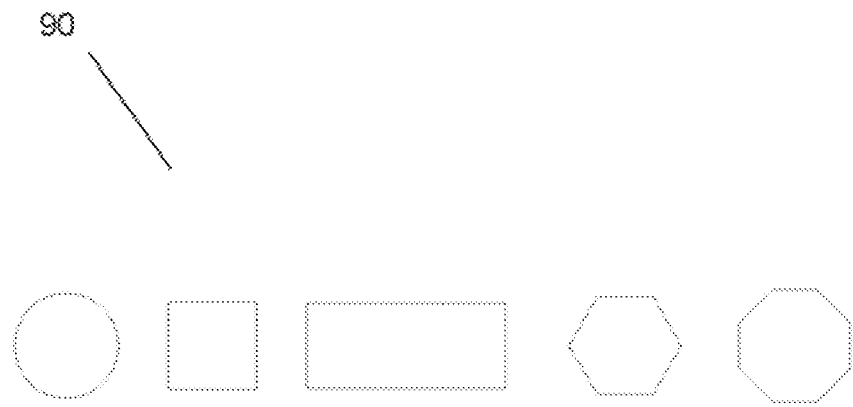
FIG. 5 shows various alternative cross sectional shapes according to different embodiments of the invention.

In various embodiments of the invention, alternative cross sectional areas for rods including but not limited to circular, square, rectangular, and multiple sided polygons such as a hexagon and octagon are shown in FIG. 5. Generally, even number of sides polygons have better spatial mixing than those with an odd number of sides although either can be used. Likewise, the optical concentrator that can be index matched to one of the rod configurations can have a similar cross sectional shape. For example a rectangular or square CPC or taper can be used. A theta by theta CPC comprised of a taper coupled to a CPC such as described by Welford and Winston ("High Collection Nonimaging Optics", W. T. Welford and R. Winston, Academic Press, 1989) can be used.

Figure 6:
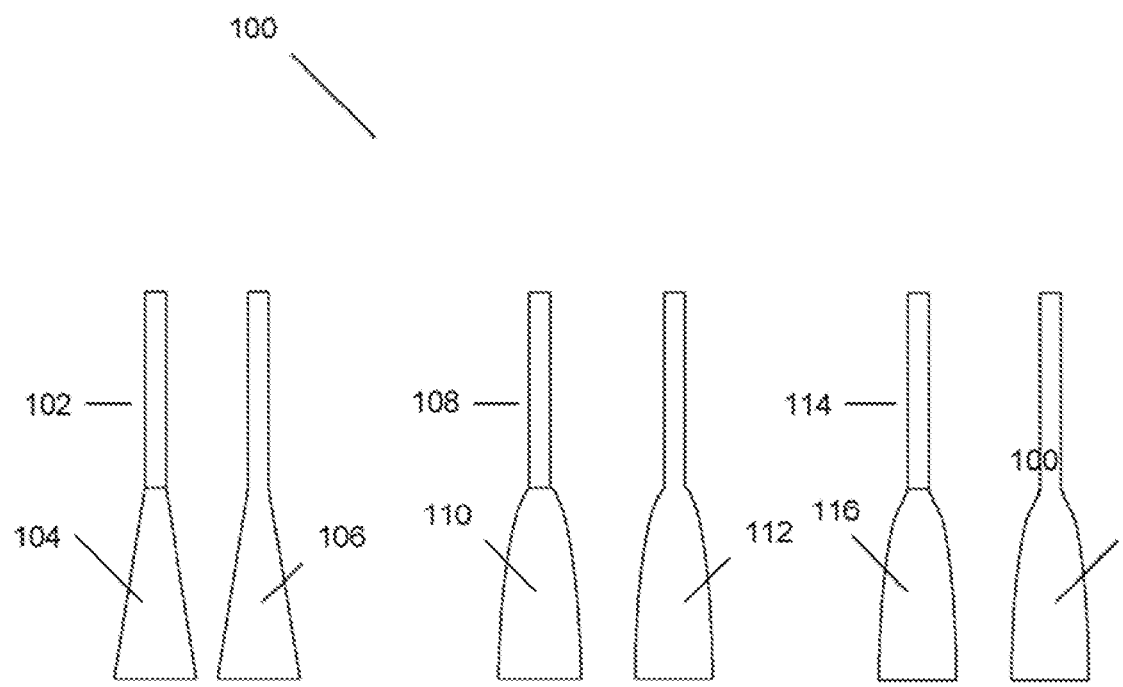
FIG. 6 shows three different output coupling optics attached to the luminescent material rod and integrated as part of the rod according to various embodiments of the invention.

FIG. 6 shows various configurations 100 of a combination of luminescent rod and output concentrators. For example the rods 102, 108, and 114, can be index matched to output couplers in the form of a taper 104, CPC 110, or combined theta by theta taper and CPC 116. In general the concentrators can be made out of a material that is transparent and of similar index of refraction and can be coupled by means of an index matching medium. Alternatively, the two components comprising a rod and concentrator can be mated by heating the components under pressure, causing them to melt together. Alternatively, the rod and concentrator can be made out of the same material such as ceramic (phosphor particles sintered at temperatures on the order of 1800° Celsius and under pressure causing the material to become transparent and substantially homogeneous) such as Ce:YAG which can be doped in the region of the rod and not doped in the region of the concentrator thereby eliminating the need for index matching.

Figure 7:
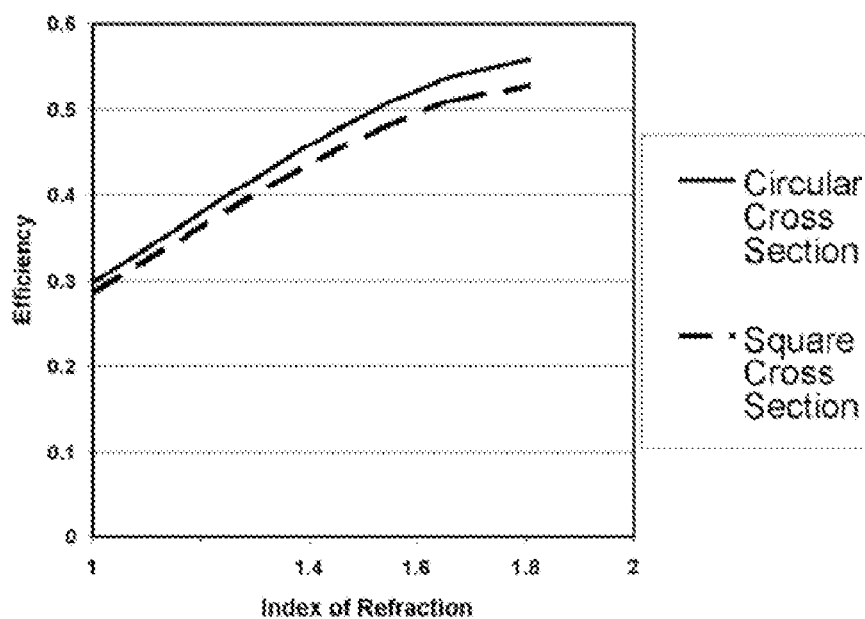
FIG. 7 shows a plot of efficiency of coupling light out of the end of the rod assuming different cross sectional shapes (_circular vs _square) as a function of the index of refraction of the attached optic.

FIG. 7 shows a plot of index of refraction of the concentrator versus coupling efficiency for the case of a Ce:YAG rod which has an index of refraction on the order of 1.82 for two rod geometries circular and square in cross section. The out-coupling efficiency into air (index of refraction 1) of 30% assumes that all the light emitted by the LED die is absorbed within the rod and that one end of the rod is coated with a mirror with reflectivity of 100%. Thus, the efficiency can be at least doubled, up to the limit of the light-guided available efficiency of about 70% for a luminescent rod having this index, by index matching to a concentrator with an index of refraction approaching that of the rod. The data assumes that the output face of the concentrator is coated to minimize losses due to Fresnel reflections at the air/glass interface.

Figure 8:
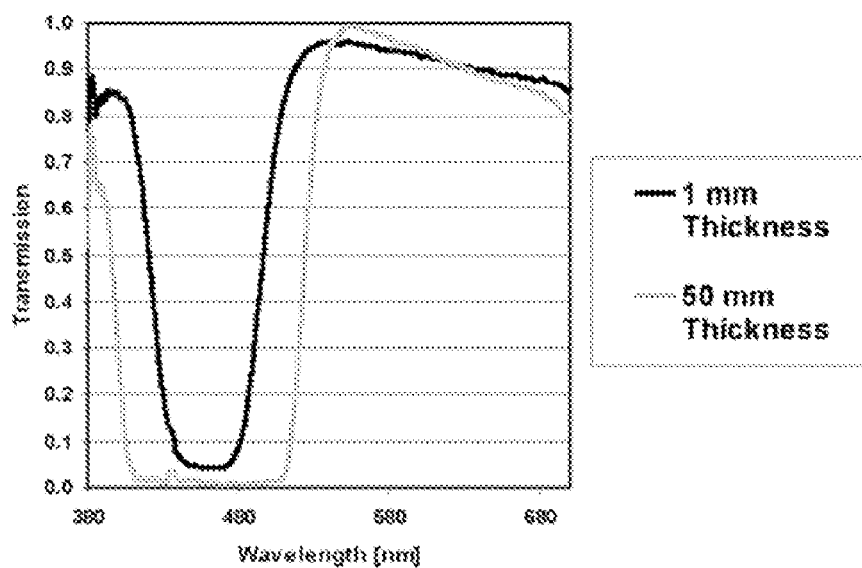
FIG. 8 shows the transmission spectrum of a white light source as a function of wavelength for two thicknesses (1 mm and 50 mm) for a 0.15% doped Ce:YAG rod.

FIG. 8 shows empirical data for a white light source transmitted through the side of a Ce:YAG rod of 1 mm thickness and guided down a length of 50 mm. The Cerium doping was 0.15%. The data shows that for the 1 mm path length more than 90% of the blue light was absorbed. The 50 mm rod was not coated, so the maximum expected transmission of blue light going into the rod would be on the order of 84% due to Fresnel reflection which is observed at a wavelength of about 400 nm where the Ce:YAG rod is substantially transparent. The fact that the output is above the expected maximum transmission for wavelengths greater than 500 nm is due to the contribution from the luminescent light emitted by the absorbed blue light in the incident white light. The broader absorption band shown in the 50 mm length is due to the fact that Beer's Law is acting over 50 times the length exponentially. It is also apparent that the material does exhibit some degree of self absorption for which some of the absorbed light emitted as phosphorescence is absorbed through the length. Thus for some applications it can be important to limit the length of the rod to minimize absorption at the short end of the emitted spectrum and to minimize heating due to self absorption.

Thermal Considerations of Rod Handling

Figure 12:
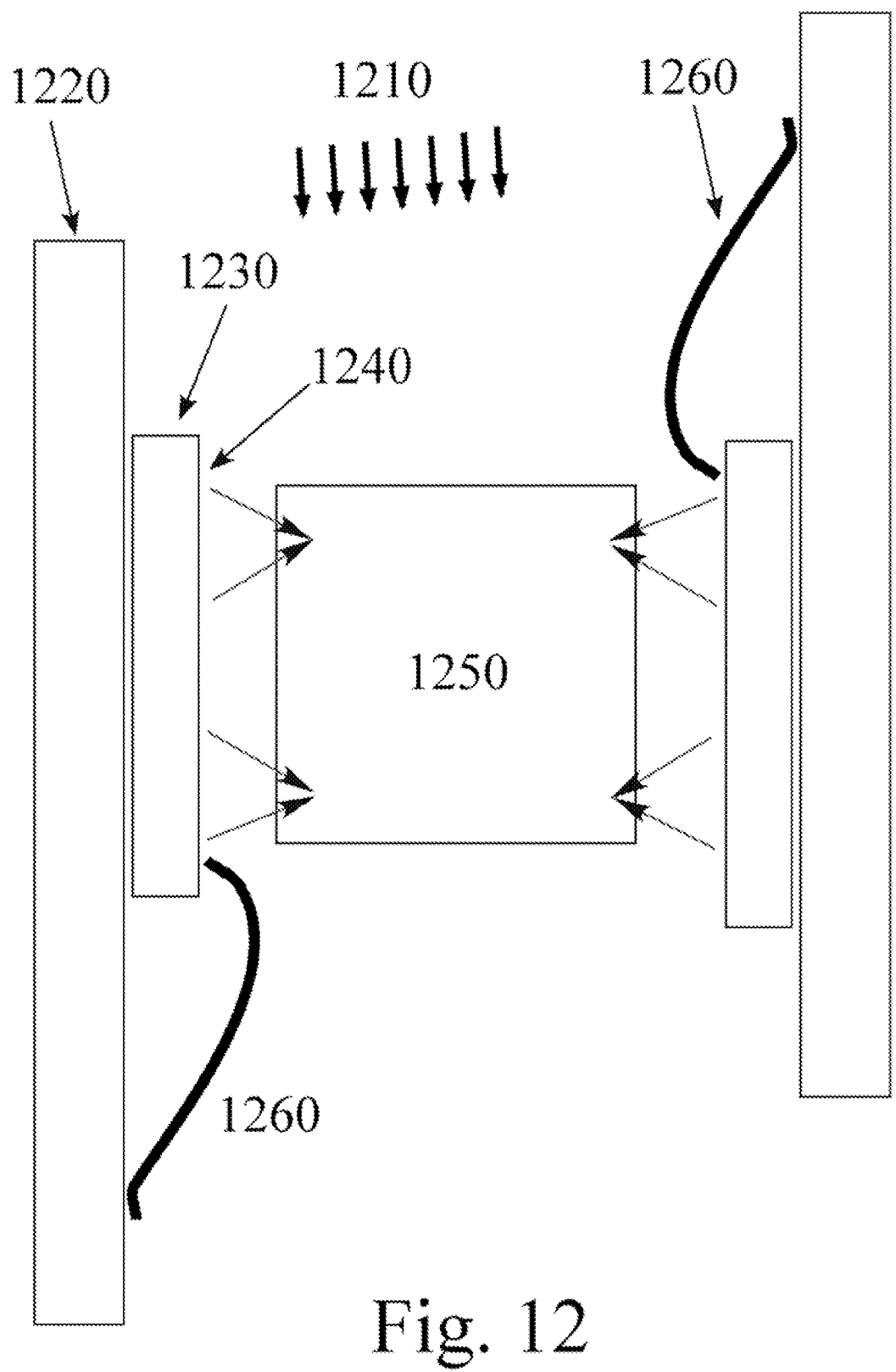
FIG. 12 an end view of a luminescent rod excited by two arrays of LEDs in which there is a column of forced air that forced between the rod and the LED surface through a controlled airspace according to an embodiment of the invention.

The rod might easily absorb 20 watts and only re-emit 15 W, due to Stokes shift and material inefficiencies, leading to a fast heating unless rather extreme cooling measures are undertaken. In an embodiment of the invention, a high pressure fan can be direct a thin column of air into the gap between opposing surfaces (LED line arrays on opposing sides) as shown in FIG. 12. The air cooling is favored if the LEDs can be spaced apart from the luminescent rod by about 200 microns (see FIG. 12).

The rod may be any shape. In an embodiment of the invention the rod is preferably square and polished highly with minimum chips so as to pass the maximum light, but without needing for example a 'laser grade' finish. The cost of the rod is high but with reduced surface tolerance specifications can be fabricated with relative ease and therefore such a component can be considered commercially viable. The density may be increased and the length of the rod shortened and cost reduced (and the spectrum consequently widened due to reduced self absorption) if the thermal load can be managed. Other methods that can be used to manage the thermal load include contacting a suitable heat-spreading material, such as a large perforated metal fin or a ceramic material placed in contact with the rod. In an embodiment of the invention, thermal consideration can be a primary concern in the overall design.

Figure 9:
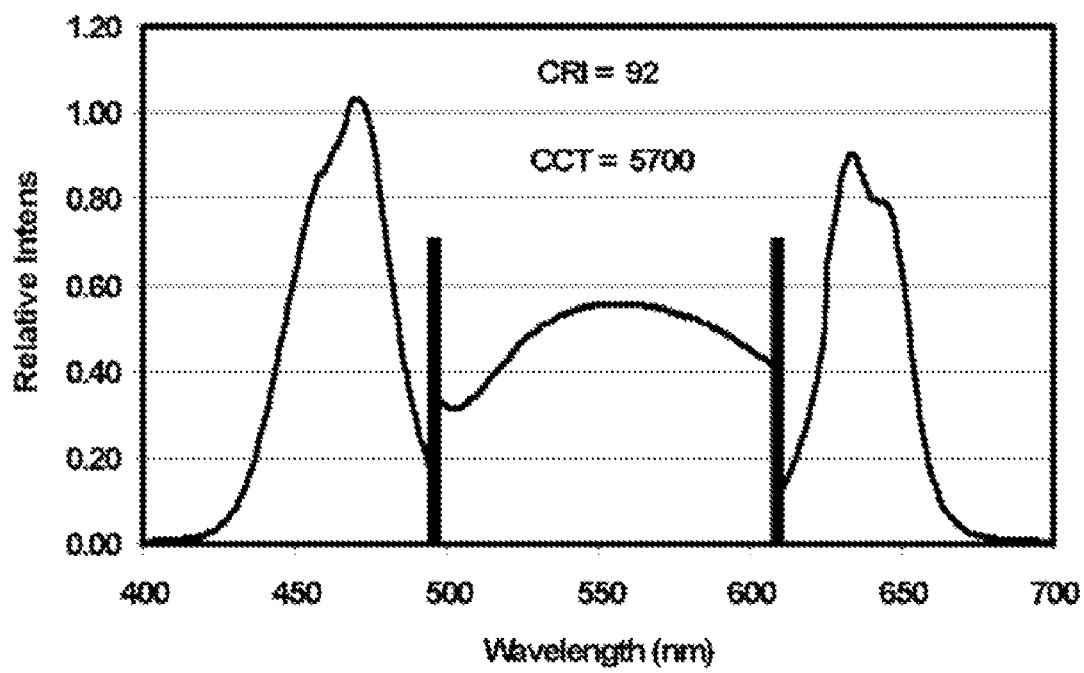
FIG. 9 shows a spectral plot of the relative intensity versus wavelength for three sources (blue, green and red) in the system of FIG. 1.

FIG. 9 shows the combined spectrum of the system of FIG. 1 with the thick black vertical lines representing the spectral region of the dichroic beam splitters. The driving current to the individual sources can be adjusted to result in a CRI greater than 90 at a CCT on the order of 5700° Kelvin which is consistent with the values typical of short arc Xenon lamps. The blue spectrum shown here is comprised of three blue LEDs with peak wavelengths centered around 445 nm, 457 nm and 470 nm. The red band is comprised of the combination of LED center wavelengths peaked near 630 nm and 650 nm. The effect of increasing the spectral widths in the blue and red spectral regions is primarily to increase the CRI.

The luminescence systems can be used for irradiating bioanalytical instrumentation including wells containing chemicals for inducing reactions or detecting reactants or products of chemical reactions. The bioanalytical instrumentation can include a light source and fiber optic systems for irradiating analytes within capillaries with selected wavelengths of light and detecting luminescence produced by the analytes within the capillaries.

Separation by electrophoresis is based on differences in solute velocity in an electric field. The velocity of a charged analyte is a function of its electrophoretic mobility and the applied voltage. The method of electrophoresis is used in a number of different techniques including capillary gel electrophoresis, capillary zone electrophoresis, micellar electrokinetic chromatography, capillary electro chromatography, isotachophoresis and isoelectric focusing.

In general, the mobility of an analyte in a particular medium is constant and characteristic of that analyte. The analytes mobility is a result of two factors. The analyte is attracted to the electrode of opposite charge, pulling it through the medium. At the same time, however, frictional forces try to prevent the analyte moving toward the charge. The balance of these forces determines the actual overall mobility of the analyte. An analytes size, polarity and number of electric charge(s), relative hydrophobicity and ionic strength determine how rapidly an electric field can move the analyte through a medium. A buffer is used to assist the flow of the analyte relative to the field. The buffer's chemical composition, pH, temperature and concentration alter the mobility of the analyte. Many important biological molecules such as amino acids, peptides, proteins, nucleotides, and nucleic acids, posses ionizable groups and, therefore, at any given pH, exist in solution as electrically charged species either as cations containing a positive (+) charge or as anions containing a negative (−) charge. Depending on the nature of the net charge, the charged particles will migrate either to the cathode or to the anode. A small analyte will have less frictional drag than a large analyte and hence move through the medium faster than a large analyte. Similarly, a multiply charged analyte will experience more attraction to the electrode and also move through the medium faster than a singly charged analyte. It is this difference in solute velocities that is responsible for the separating effect in electrophoresis that results in resolution of the species detected.

Gel electrophoresis is a method that separates molecules such as DNA or proteins on the basis of their physical properties. A gel is a solid colloid. Thus, gel electrophoresis refers to the technique in which molecules are forced to cross a span of gel, motivated by an electrical current. Activated electrodes at either end of the gel provide the electric field and thus the driving force for the migration of the analyte. During electrophoresis, molecules are forced to move through the pores in the gel when the electrical current is applied. Their rate of migration, through the induced electric field, depends on the strength of the field, their charge, their size and the shape of the molecules, the relative hydrophobicity of the molecules, and on the ionic strength and temperature of the buffer in which the molecules are moving.

One use of gel electrophoresis is the identification of particular DNA molecules by the band patterns they yield in gel electrophoresis, after being cut with various restriction enzymes. Viral DNA, plasmid DNA, and particular segments of chromosomal DNA can all be identified in this way. Another use is the isolation and purification of individual DNA fragments containing interesting genes, which can be recovered from the gel with full biological activity.

Capillary Zone Electrophoresis (CZE) replaces the gel in gel electrophoresis with the combination of a buffer and a solid support contained within the capillary. In CZE, the analyte must move through the solid support contained within the capillary under the action of the buffer, which is charged by the applied electric field. The buffer's chemical nature, pH, temperature, concentration and the presence of surfactant additives can be selected to assist in fully resolving (i.e., spatially separating different analytes in the capillary with respect to the time from introduction of the sample) different analytes in space (position in the capillary) with respect to time. Analytes separated by CZE can be detected based on absorption or fluorescence. Detection can be carried out using on-column or fiber optic Z-cells.

In addition to electrophoretic techniques, separation of molecules can be carried out in the absence of an applied field using chromatographic techniques. In liquid chromatography, the molecule dissolved in a buffer can still be charged, but rather than an electric field creating the driving force, molecule migration is dependent on the flow of the buffer. Frictional forces due to the interaction of the molecule with a solid support present in a column, act to prevent the molecule from moving with the buffer. The molecule's size, hydrophobicity, and ionic strength determine how rapidly the buffer can move the molecule through a medium. The buffer's chemical composition, pH, temperature and concentration together with the nature of the solid support dispersed in the column alter the mobility of the molecule. High performance liquid chromatography (HPLC) utilizes pumps to increase the flow of buffer through the columns resulting in high column backpressure, improved resolution, increased flow rates and reduced analysis times. By reducing the diameter of the column and/or increasing the length of the column the resolution can be improved. However, a problem with narrower columns (milli bore or micro bore) involves detection of the eluted species. As the diameter of the capillary in the narrow bore HPLC systems is further reduced, only a small number of molecules are available for detection in a small-defined area.

Microfluidic systems comprised of microfluidic chips, automated reagent delivery apparatus and detection instrumentation are designed to minimize the users' effort in reagent delivery, reagent dilution and/or mixing, initiating chemical reactions and detecting those chemical reactions in small volumes within highly automated environments. Among the numerous applications that exist, fluorescence is a commonly used detection format. It is a sensitive and robust method for detecting enzyme assays, immunoassays, polymerase chain reaction (PCR), quantitative PCR, genomic sequencing among many other important chemical reactions. Both homogeneous and heterogeneous reactions are suited to such devices and analysis is not limited by whether the reaction takes place in free solution or on a solid support or within a narrow pore. Often microfluidic devices are produced by etching, molding or embossing channels and wells into solid substrates (glass, silicon, plastic, etc.). Numerous layers of the device can be fabricated and then the layers assembled to form the final analysis tool. Channels can be etched in single or multiple dimensions enabling more complicated chemical separation and detection. Such devices can be used to introduce reagents directly onto the chip or interfaced with automation equipment for such purposes. Like all fluorogenic detection, these systems require an excitation source.

The present invention consists of one or more light sources in the form of a luminescent light pipe referred to herein as a lamp, in conjunction with relay optics for luminescence collection from an analyte forming a luminescence system for a volume interrogation apparatus wherein the interaction of light with a chemical species located within or supported on a solution volume can be the measure of the presence or quantitation of an analyte. Luminescence is defined as light not generated by high temperature alone, typical of incandescence, including but not limited to fluorescence and phosphorescence. Where high temperatures are defined as above approximately 2000° K. The analyte can be part of a reaction involving species including biopolymers such as, oligonucleotides (DNA, RNA iRNA, siRNA), proteins (including antibodies, enzymes, agonists, antigens, hormones, toxins), oligosaccharides and non polymeric species such as steroids, lipids, phospholipids, small organic signaling molecules (e.g., retinoic acid), pesticides and non peptidic toxins, hormones and antigens.

In alternative embodiments of the present invention, a luminescence system in conjunction with relay optics for luminescence collection, form a flexible and efficient system for a capillary/fluorescence apparatus. In an embodiment of the invention, a plurality of light sources and fiber optic systems separately and simultaneously irradiate a plurality of capillaries with selected wavelengths of light and the fluorescence produced by the molecules flowing within the capillaries can be separately and simultaneously detected. 'Simultaneously' is herein defined as occurring close in time. Two light pipes can irradiate two capillaries at the same time and the fluorescence from the molecules in one of the capillaries can be delayed due to physical or chemical effects relating to absorption, phosphorescence and/or fluorescence resulting in a delay in the fluorescence from the molecules in one of the capillaries.

In an embodiment of the present invention, a luminescence and collection system can be adjusted for uniform luminescence of multiple capillaries or wells or a large area including numerous wells, spots or channels as 'detection volumes'. In an embodiment of the present invention, luminescence systems can irradiate an array of channels in an array of capillaries. In an embodiment of the present invention, an array of channels can be etched, molded, embossed into the capillaries. In an embodiment of the present invention, a set of wells intimately connected to fluidic conduits can be stepped along the length of the fluidic conduit such that they can be interrogated at numerous sites for the purposes of creating a map or image of the reacting species.

In an embodiment of the present invention, a luminescence and collection system can irradiate an array of wells, spots and or an array of channels (be they etched, molded or embossed) or a set of wells intimately connected to fluidic conduits such that they can be interrogated at numerous sites for the purposes of creating a map or image of the reacting species.

In an embodiment of the present invention, a luminescence and collection system can irradiate homogeneous reactions within fluidic conduits or reservoirs; to irradiate heterogeneous reactions on the surface of fluidic conduits or reservoirs; to irradiate homogeneous or heterogeneous reactions on the surface of or within the pores of a porous reaction support.

In an embodiment of the present invention, a luminescence and collection system can emit multiple colors as desired. In an embodiment of the present invention, a luminescence and collection system can be pulsed on and off as desired to reduce heat generation. In an embodiment of the present invention, a luminescence and collection system can be pulsed on and off to allow time-based fluorescence detection.

In an embodiment of the present invention, a luminescence and collection system can detect one or a number of reactions within the detected volume or volumes. The narrow band source of the light pipe driven analyzer provides better specificity, higher sensitivity, and lower backgrounds signals. The light pipe driven analyzer easily accommodates multiple wavelengths by additions of serially connected components.

In an embodiment of the present invention, a luminescence and collection system can be pulsed on an off as desired to reduce or control heat generation and to allow time-based fluorescence detection.

In an embodiment of the present invention, luminescence systems can irradiate homogeneous reactions within fluidic conduits or reservoirs. In an embodiment of the present invention, luminescence systems can irradiate heterogeneous reactions on the surface of fluidic conduits or reservoirs. In an embodiment of the present invention, luminescence systems can irradiate homogeneous or heterogeneous reactions on the surface of or within the pores of a porous reaction support.

Figure 14:
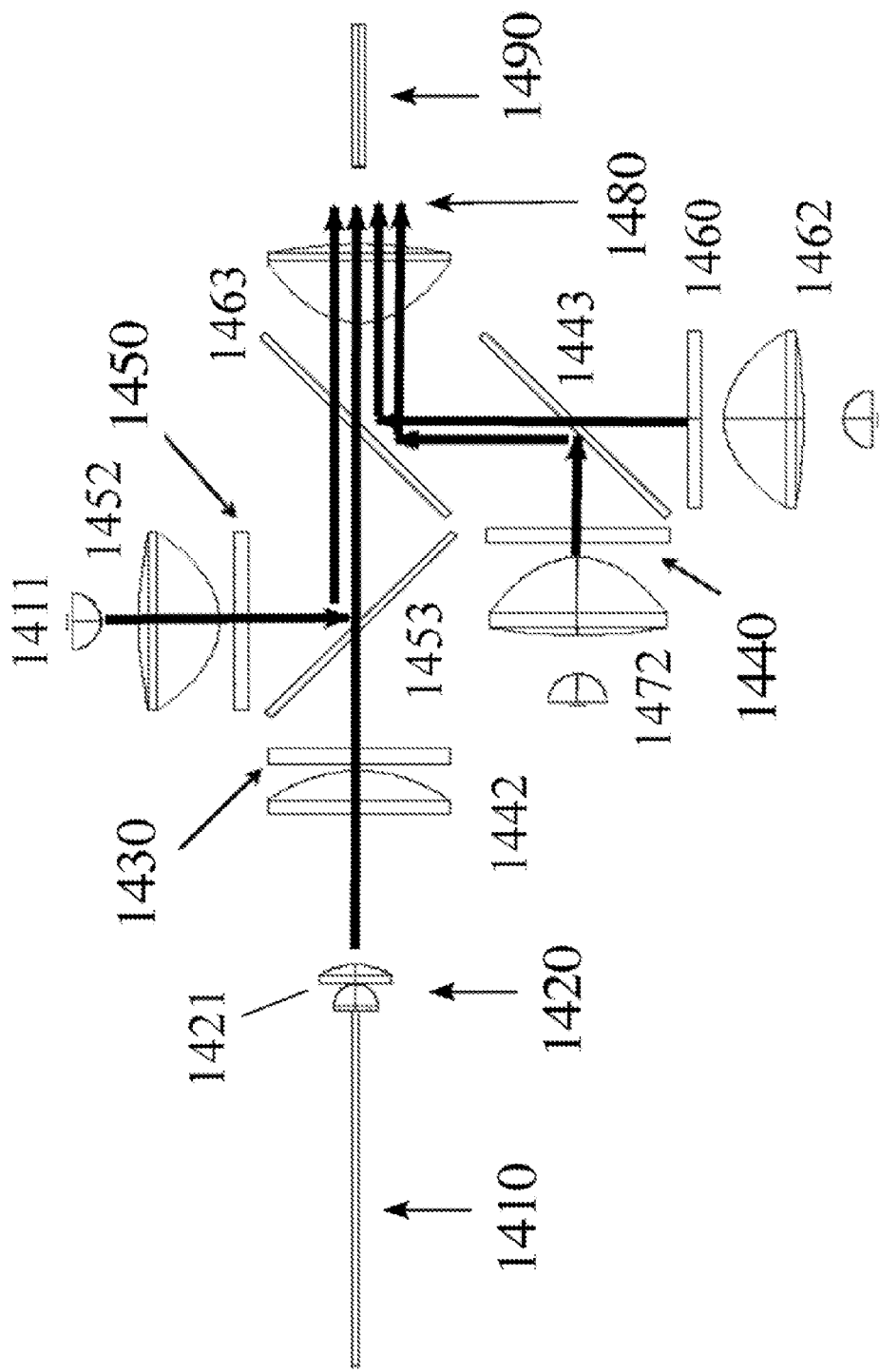
FIG. 14 shows a four color light engine layout, including a luminescent rod and three other solid state light sources, with dichroic mirrors to create a single coaxial 4-color beam. Each individual light source is collimated so as to be efficiently combined and after color combination the beam is refocused into a light guide for transport to the device or system to be illuminated according to an embodiment of the invention.

The light engine can be constructed to generate one or more colors. FIG. 14 illustrates a four color light engine consisting of LEDs 1411 and a luminescent rod 1410. The output of each light source is filtered to generated the specified spectral band using a band pass filter 1430, 1440, 1450 and 1460 and then combined into one common optical path using dichroic filters 1443, 1453, and 1463 positioned at 45 degrees. The output from the rod is first out coupled using a truncated ball lens or other light extracting element 1420 and magnified by a plano convex lens 1421. This light is then collimated by a asphere plano convex lens 1442. Similarly the output from the other light sources is collimated using aspheres 1452, 1462, and 1472. The asphere lenses are designed so that the collimated light is generated and can pass through the bandpass filters at nearly normal incidence, a requirement for optimum filter performance. The light exits the light engine through a liquid light guide 1490. Other embodiments include a optical adapters suitable for critical illumination and Kohler illumination.

Figure 10:
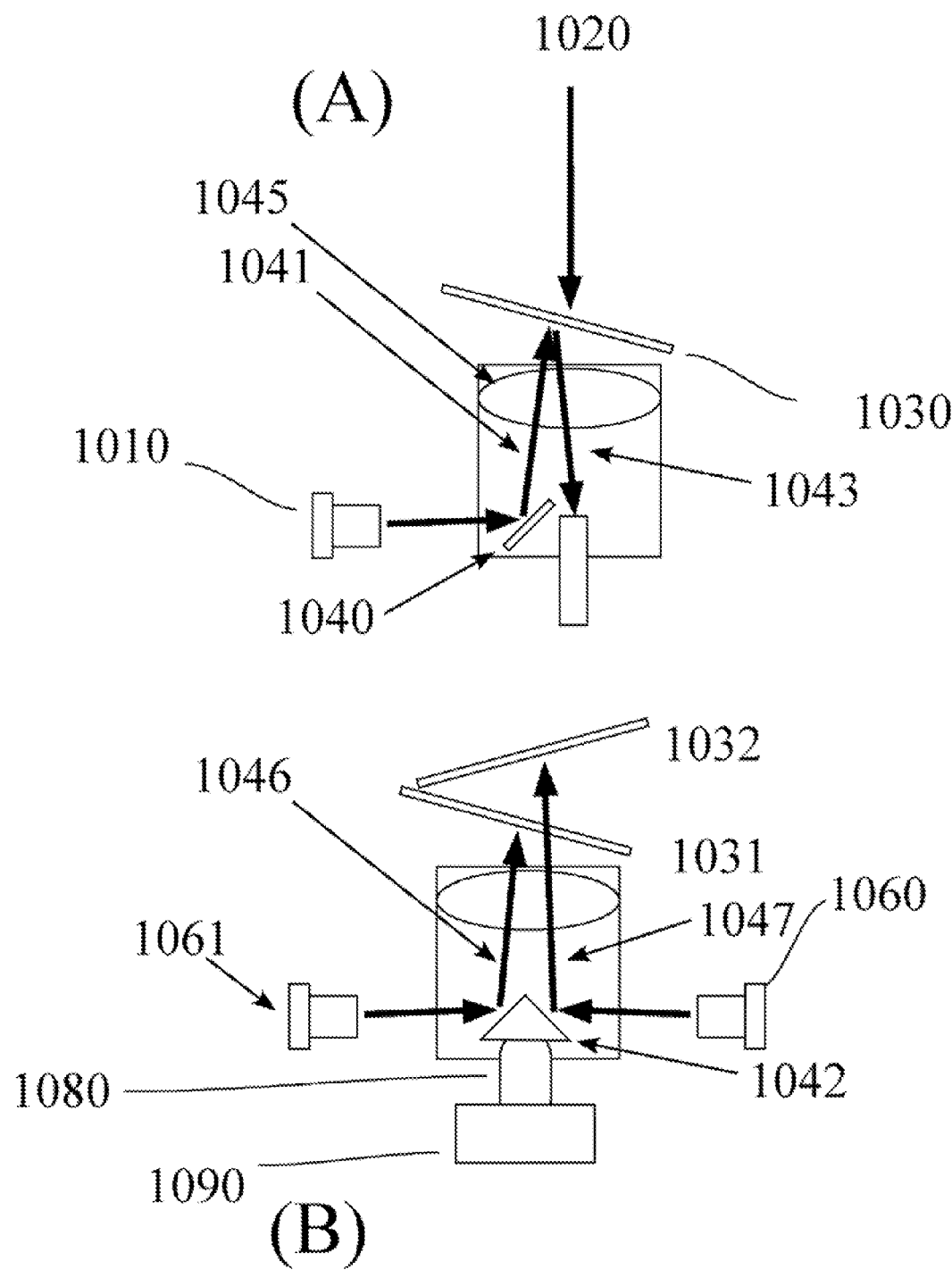
FIG. 10 shows a means of combining (A) a laser beam, specifically a direct laser diode, with the other colors in order to increase the color palette of a light engine, and (B) two laser beams, according to an embodiment of the invention to create a 6 color light engine (see FIG. 13)
Figure 13:
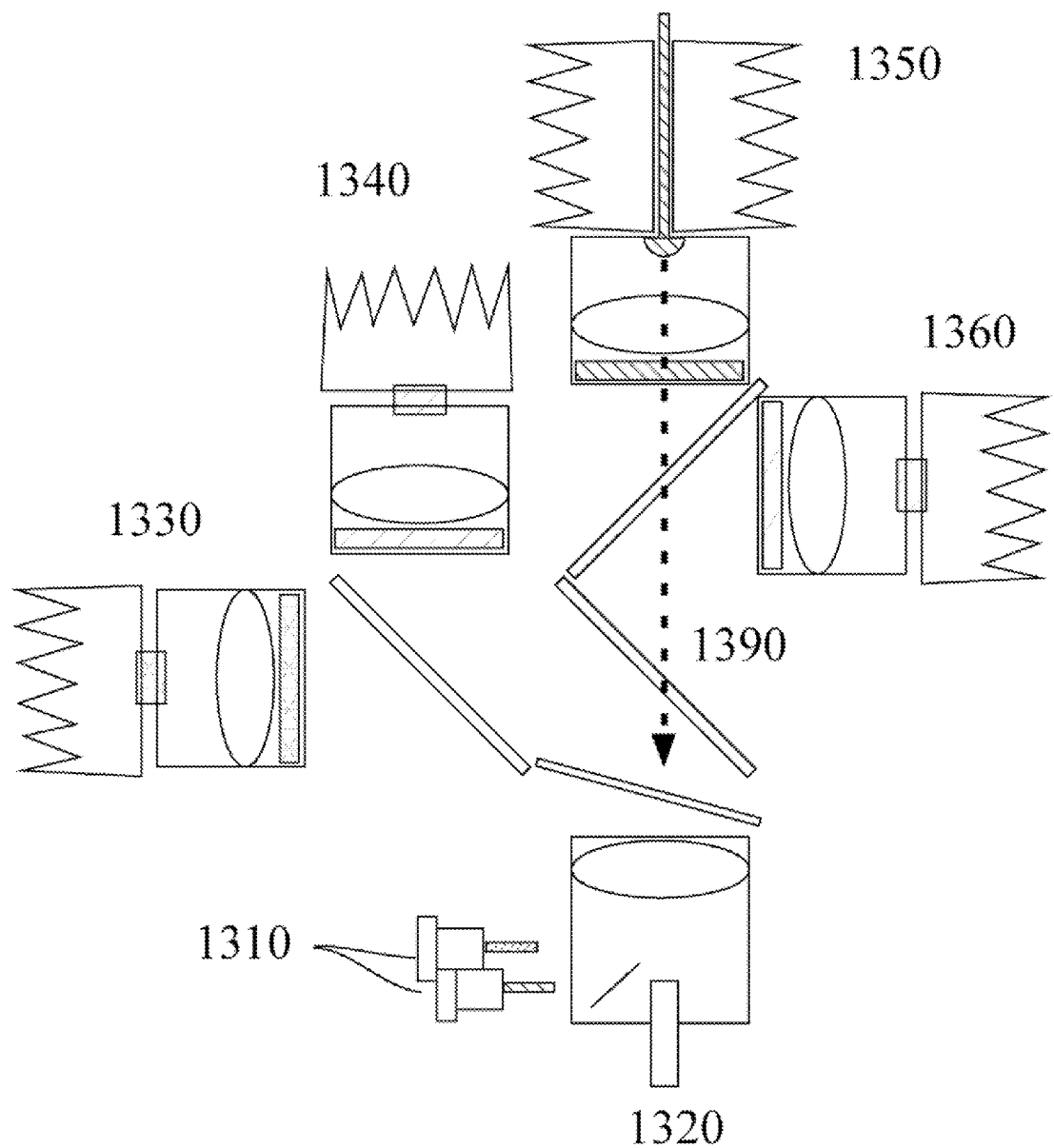
FIG. 13 shows a six color light engine layout, including a luminescent rod, two laser diodes and three other solid state light sources, with dichroic mirrors to create a single coaxial 6-color beam according to an embodiment of the invention.

In FIG. 13 an embodiment is shown for a six color engine. A blue LED and collimating optic 1330 is combined with a yellow LED and collimating optic 1360 and a cyan LED and collimating optic 1340 and these three wavebands combined with a luminescent rod and its associated collimating optic 1350, where only the light emitted by the luminescent rod 1350 is shown as beam 1390 (dotted line). Such four color combination is further combined with two laser diodes 1310 and all six color bands focused into a light guide 1320 as described in FIG. 10.

Referring to FIG. 10(A), a laser diode 1010 which might be preferably selected from a wavelength range of 630 to 650 nm, is pointed at a small mirror 1040 to direct the light 1041 substantially in the opposite direction from the main optical axis 1020 of the light engine. Said main optical axis 1020 already contains at least one color component such as will be generated by using a luminescent rod excited by LED sources. In one embodiment the red laser diode beam shape is sufficiently wide to cover a substantial portion of the collimator lens 1045 and the distance of the divergent laser beam is substantially equal to the focal length of such collimating lens. The collimator may be a molded aspherical lens to reduce spherical aberrations. Directly thereafter the collimated red laser beam strikes a dichroic mirror 1030 which is tilted slightly, in the range of 2 to 8 degrees so as to redirect the laser beam back into the collimating lens 1045, at near normal incidence, i.e. superimposed 1043 and collinearly with the main optical axis 1020 of the light engine. The red light is reflected at least 95% by said dichroic mirror, which passes substantially all of the main light engine beam, including at least 90% of the filtered light that may result from utilizing a luminescent rod with a green or yellow narrow passband filter. The edge steepness of the dichroic is particularly sharp because of the near perpendicular usage of this edge filter. Such kinds of dichroic mirrors are less ideal at, for instance 45 degrees where polarization effects and angular walk-off cause poor edge steepness, so this construction has particular advantages for efficient color combination of multiple color bands.

Referring to FIG. 10(B), two laser diodes 1060, 1061 can be combined as explained in FIG. 10(A), and the small apparent source size allows these beams to be combined by a knife-edge (prism) 1042 such that both beams 1046, 1047 can be refocused using dichroic mirrors 1031, 1032 into a suitably large light guide. For instance a 2 mm prism can be used with two red laser diodes 1060, to spatially combine the two sources (which may have different or identical wavelength output) into a 3 mm diameter entrance of a liquid light guide. An alternative embodiment can use a larger prism with apparent source positions coming from both sides of the optical centerline such that two different wavelength laser beams can be directed toward the collimator lens, and after that, two different dichroic mirrors utilized to reflect the two independent lasers back into the main optical axis, collinearly and overlappingly. For example a 405 nm laser diode can be directed as in FIG. 10(A), but from the opposing side and with a tilted dichroic, at an opposite tilt angle as shown in FIG. 10(B). In one embodiment a small prism is used to spatially combine two different wavelength laser diodes, such that they can both be condensed, i.e. refocused, into the same light guide. In a further refinement of the method, the prism combiner is mounted including some mechanical means 1080 onto a vibrating element 1090 such as an audio transducer or piezo element or the like, which imparts sufficient disturbance to both laser beams so as to cause a disruption of the inherent speckle pattern to increase the uniformity and usefulness of the illumination for certain critical illumination applications.

In an embodiment of the invention, the two laser diodes combined can be of different colors. In an alternative embodiment of the invention, the combining can be with a colored prism, holographic or other dichroic.

Notably each of the independent laser diodes can be directly modulated, turned on and off at high speed. It is also contemplated that a bandpass filter or other optical element can be inserted between each laser and the combining elements, for instance a heat rejection filter, to further improve the light source for suitability for any intended application.

Optical Extraction Efficiency

Figure 11:
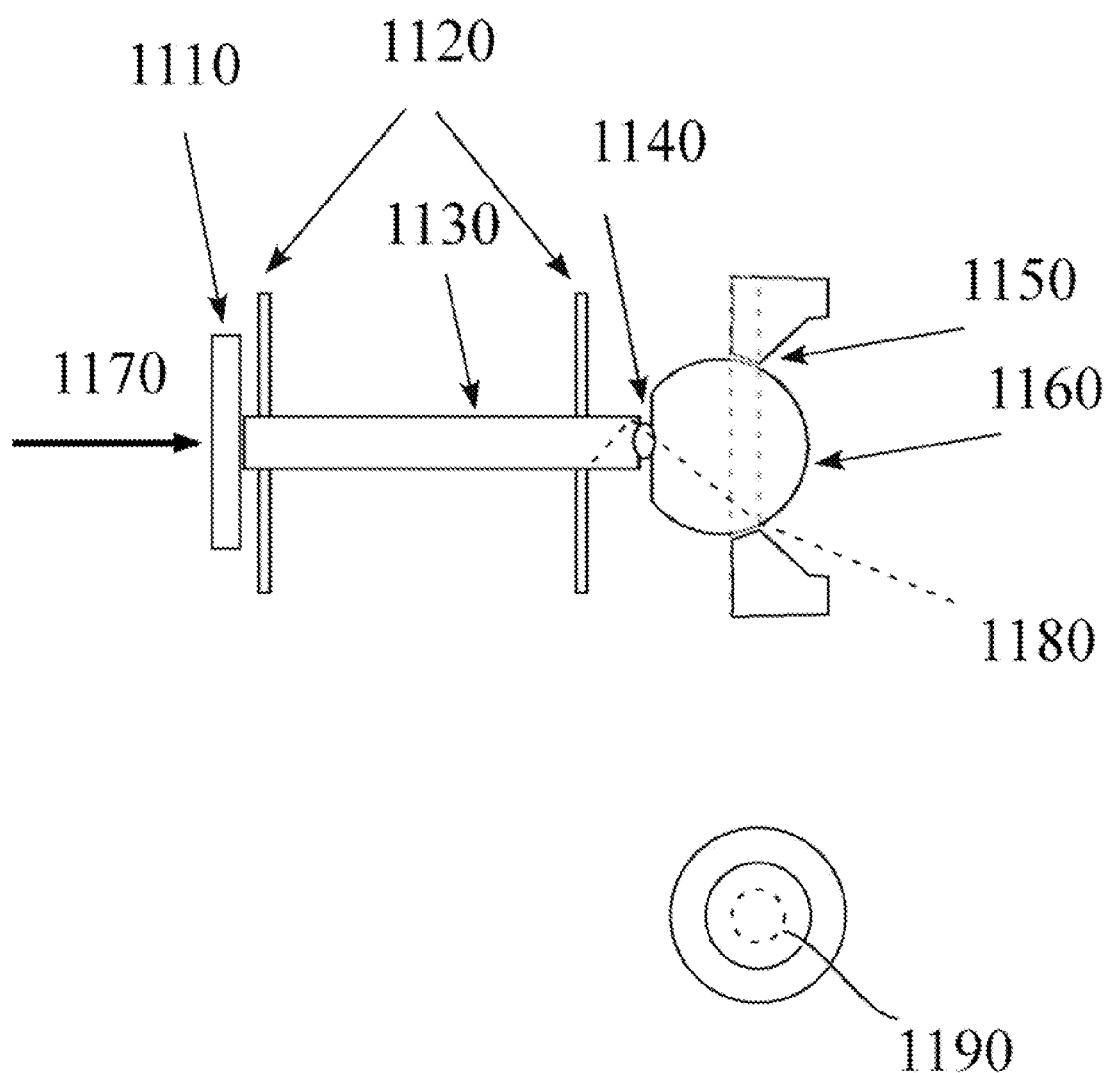
FIG. 11 shows a truncated ball lens for coupling to a luminescent rod according to an embodiment of the invention.

In an embodiment of the invention, if the rod is coupled to the same or similar index material then it is logical to 'outcouple' through a dome. FIG. 11 shows a side view of the luminescent rod 1130, where a mirror 1110 is positioned at one end of the luminescent rod 1130, and brackets 1120 constrain the rod 1130. Luminescence (dotted line) 1180 from the rod 1130 exit the aperture and the coupling gel 1140 through the conical seat 1150 and the dome 1160 along the main axis compressive force 1170. In a frontal view, the dome is shown with the truncated ball lens 1190. In such an embodiment, if the dome is sufficiently larger, on the order of 3 to 20 times larger in diameter than the rod cross-section, the light will escape normal to the ray within the crystal and emission of about 57 degree half angle can be expected for instance for YAG:Ce. Out-coupling is defined as application of the same or similar index material that is 3 to 20 times larger in diameter than the rod cross section, which can be shaped like a dome.

An unexpected result can be obtained with a modest index (n approximately 1.4 to 1.6) coupling gel or epoxy. In this context approximately corresponds to ±0.1. The thin layer is held in place by direct compression via a back mirror (using the same or similar coupling material if needed) and a spring. The mirror and ball lens are centered on the crystal. The extraction is further enhanced if a truncated ball lens is employed. A truncated ball which is of a slightly higher index than the crystal and which spacing is exactly set by its tolerances of thickness allows the 57 degree internal half angle rays to come out at 45 degrees (nominally) and be more easily collected and utilized.

FIG. 12 shows an end view of a luminescent rod 1250 excited by two arrays of LEDs 1230 in which there is a column of forced air 1210 that forced between the luminescent rod 1250 and the LED surface 1240 through a controlled airspace according to an embodiment of the invention. The LED 1230 is bonded to a metal core circuit board 1220 which acts as a heat sink and a wire bond 1260 between the LED 1230 and the circuit board 1220.

In an embodiment of the invention, the magnification can then be further optically corrected to a perfect collimation, which can be color-combined using standard dichroic edge combiners and recondensed to a spot. In an embodiment of the invention, the spot can be a liquid light guide. In an alternative embodiment of the invention, the spot can be a fiber bundle. In another embodiment of the invention, the spot can form the pupil of a Kohler illuminator.

In an embodiment of the invention, a desirable high efficiency and highly effective illumination system for fluorescent microscopy can be formed by this color combined section in combination with the optics for Kohler adaptation.

In an embodiment of the invention, the etendue of a single LED can be perfectly matched to the etendue of a liquid light guide. Assuming 1×1 mm LED and 3 mm entrance guide, the numerical aperture (NA) can be in the range from 0.2 up to about 0.6 which can be coupled to the microscope by said Kohler adapter. In an alternative embodiment of the invention, the image of the lightsource at the refocused spot can be scrambled or made homogeneous by means of a integrating or mixing rod or a mirror tunnel, which can be then be used within an Abbe illumination system.

Many other applications exist for a portable, directly computer controllable, easily spectrally tunable (by filter selection) light sources of medium to very high brightnesses.

The distance between lenses in the Kohler setup is 95 mm and from LE output to Isuzu is 10 mm (1 mm shorter than the natural BFL).

EXAMPLE 1

In an embodiment of the invention, a rod with 0.8 mm square cross-section is coupled to a truncated ball lens and further magnified by a small plano-convex lens, finally collimated by a 38 mm focal length (FL) asphere. Allowing for two dichroic combining mirrors leaves an air space of 68 mm. The energy can be refocused with another asphere, into a 3 mm liquid light guide with an effective 0.3 NA.

FIG. 14 shows that at the refocus, a rectangular image of about 3.6 mm square is obtained; appropriate for alignment and optical tolerance buildups.

Figure 15:
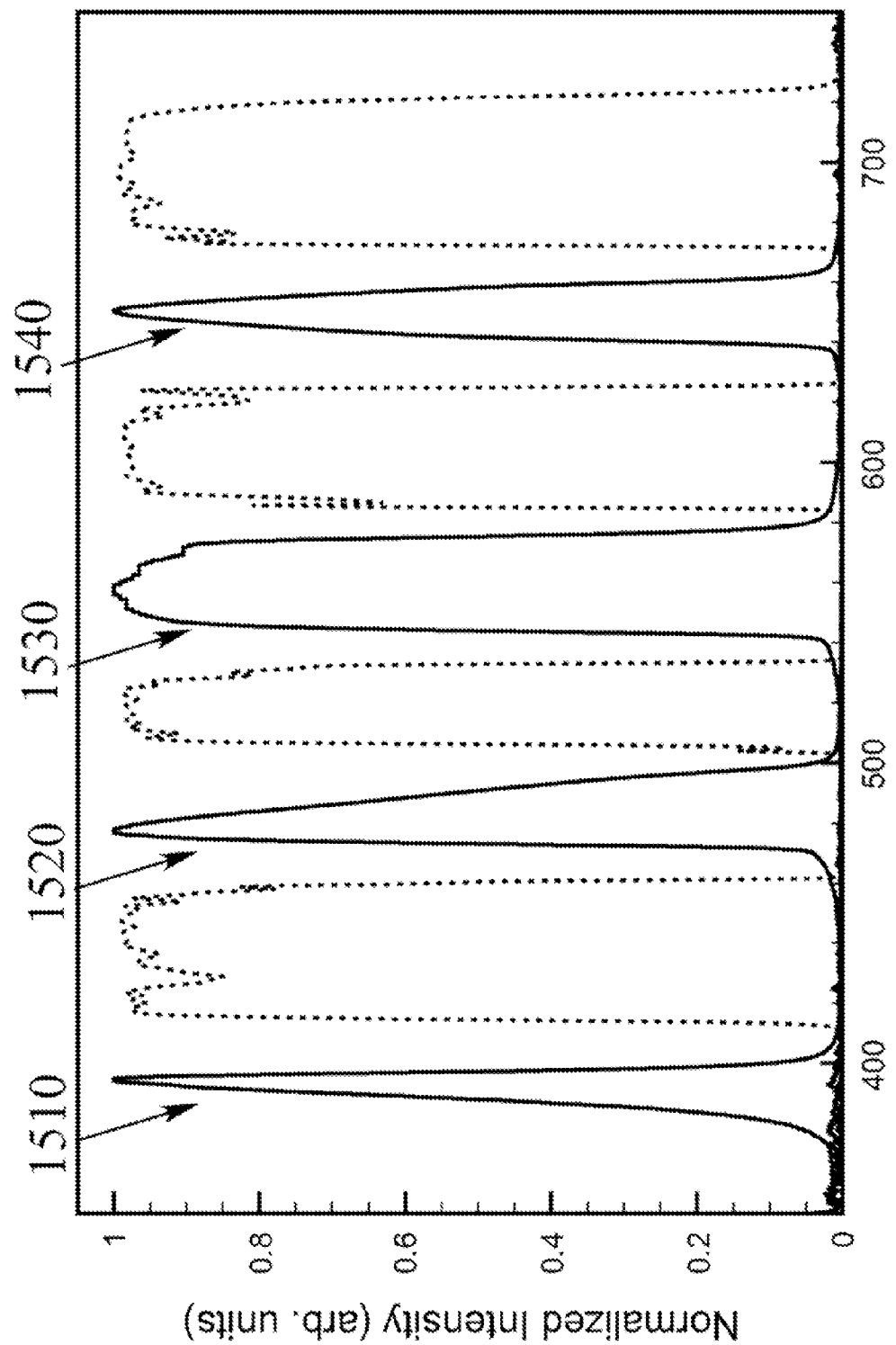
FIG. 15 a resulting spectrum with four color bands combined alongside a standard fluorescence microscopy emission filter, according to an embodiment of the invention which provides narrow band illumination regions that do not overlap with the spectral regions of interest to bio-analysis.

FIG. 13 shows that launching rays within 55 degrees in the YAG, 40% can be transferred into the LLG. In FIG. 15, a representative output from a four color light engine is provided. The specific colors (solid line) shown are UV 1510 (395 nm), 1520 Cyan (485 nm), 1530 Green (560 nm), and 1540 Red (650 nm). Such a range of colors can be generated by a combination of diode lasers, LEDs and luminescent light pipes. The band positions and bandwidths for each color can be adjusted for a specific application. The output can consist of just color or a mix of colors turned on in any order with any intensity for any length of time. The output of the light engine can be used to excite any fluorescent label. The specific colors shown are particularly well suited to excite DAPI, FITC, Cy3 and Cy5, respectively, because these colors overlap well the absorption bands of the labels. Other dyes can also be excited by these colors. The light engine can be engineered to generate a different mix of colors needed to excite labels with different absorption bands.

In standard fluorescence analysis, the emission from each label is filtered by an emission filter before being recorded by a detector such as a CCD camera. In FIG. 15, the profile for a four band emitter is shown (dotted line). The spectral output of the light engine is precisely aligned with the emission filter so that the labels are excited and fluorescence is detected with maximum signal to noise.

Figure 16:
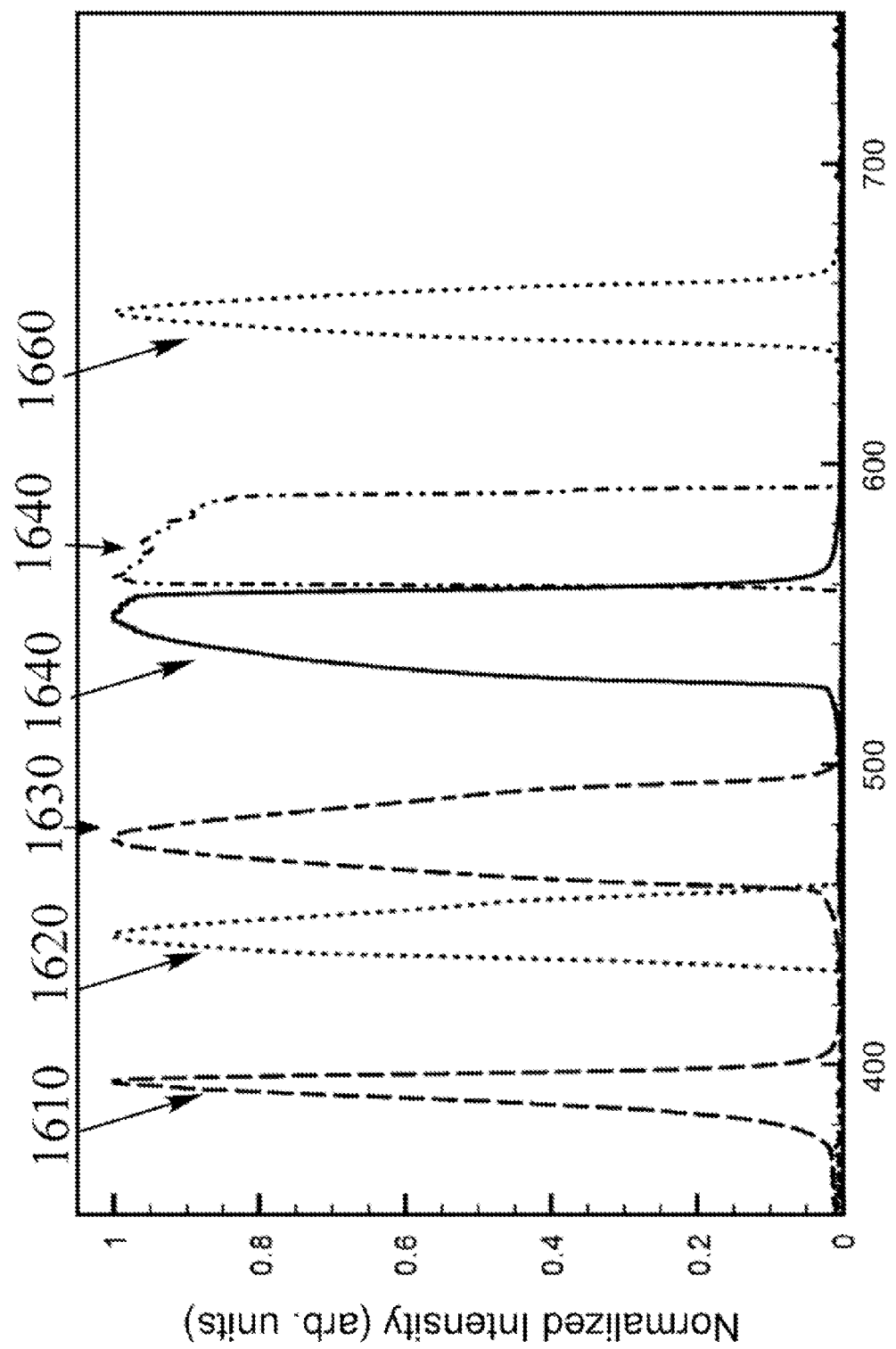
FIG. 16 shows a six color result, according to an embodiment of the invention to realize a versatile light engine for life science analysis with narrow bands spread across the visible spectrum with nearly the same optical energy available in each band.

The output of the light engine can be engineered for a specific emission band filter or collection of emission band filters to realize maximum signal to noise. Maximum signal is achieved by maximizing the fluorescence signal level which is due the absorbance of the excitation light and bandwidth of the emission filter. Minimum noise is realized by incorporating bandpass filters in the light engine (shown in FIG. 14). In this manner, the excitation light is typically reduced by 6 to 12 orders of magnitude at the detector FIG. 16 shows a representative output from a six color light engine according to an embodiment of the invention (FIG. 13). In FIG. 16, the specific colors shown are 1610 UV (395 nm), 1620 Blue (445 nm), 1630 Cyan (475 nm), 1640 Green (542 nm), 1650 Yellow (575 nm) and 1660 Red (650 nm). In various embodiments of the invention, a range of colors can be generated by a combination of diode lasers, LEDs and luminescent light pipes. In various embodiments of the invention, the band positions can be adjusted for a specific application. In various embodiments of the invention, the bandwidths for each color can be adjusted for a specific application. In various embodiments of the invention, the output can consist of just color or a mix of colors. In various embodiments of the invention, the output can be turned on in any order for any length of time. In various embodiments of the invention, the output intensity can be varied for any length of time.

The far field (1 m distant) shows that an NA of about 0.31 can be filled.

The etendue of the rod is approximately 4.74 whereas the etendue of the target liquid light guide, restricting the NA output to 0.30 is a value around 1.9. A collection efficiency of 40% is the most which can be expected. The rod is slightly oversized (86% is the maximum for circular collection from a square).

The breadth and scope of the present invention should not be limited by any of the above-described exemplary embodiments, but should be defined only in accordance with the following claims and their equivalents.

What is claimed is:

1. A fiber optic illumination system, comprising:
   a first LED light source, wherein the first LED light source emits a first light of a first color wherein the first color is a color other than green; and
   a luminescent rod light source, wherein the luminescent rod light source includes
      a second LED light source comprising a linear array of LEDs, wherein the second LED light source emits blue light, and
      a luminescent rod having a straight longitudinal surface parallel to said linear array of LEDs such that the luminescent rod is positioned to receive the blue light, wherein the blue light is absorbed by the luminescent rod which then generates by luminescence and emits green light;
      the luminescent rod having an outlet aperture wherein the green light exits the luminescent rod at the outlet aperture;
   a liquid light guide adapted to couple the fiber optic illumination system to a fiber optic device; and
   associated optics that combines the first light of the first light source with the green light generated by the luminescent rod into a combined light beam on a same optical axis and focuses said combined light beam into said liquid light guide.

2. The fiber optic illumination system of claim 1, further comprising a third LED light source that emits red light; and
wherein the associated optics combines the red light of the third light source with the first light of the first light source and the green light generated by the luminescent rod into a combined light beam on the same optical axis.

3. The fiber optic illumination system of claim 1, further comprising a light pipe to couple the combined light beam to a system that uses one or both the first light and the green light of the illumination system.

4. The fiber optic illumination system of claim 1, further comprising a reflective element positioned at one end of the luminescent rod to reflect green light towards the outlet aperture.

5. The fiber optic illumination system of claim 1, wherein the first LED light source includes a plurality of LEDs, and the second LED light source includes a plurality of LEDs.

6. The fiber optic illumination system of claim 1, wherein the associated optics includes a combination of collimator and dichroic mirrors.

7. The fiber optic illumination system of claim 1, wherein the luminescent rod is out-coupled through a dome or similar shaped structure made of a material having a substantially similar index of refraction as the luminescent rod.

8. The fiber optic illumination system of claim 1, wherein the second LED light source comprises a plurality of linear arrays of LEDs, the plurality of linear arrays positioned parallel to the luminescent rod with the LEDS no greater than 200 microns from the rod.

9. The fiber optic illumination system of claim 1, wherein the luminescent rod comprises one of a single crystal Ce:YAG rod and a sintered ceramic Ce:YAG rod.

10. The fiber optic illumination system of claim 1, further comprising:
a third LED light source that emits red light,
wherein the first light emitted by the first LED light source is blue light; and
wherein the associated optics combines the red light of the third light source with the blue light of the first light source and the green light generated by the luminescent rod into a combined light beam on the same optical axis.

11. A method of generating illumination using a fiber optic illumination system, comprising the steps of:
applying a first potential to a first light source, wherein the first light source is selected from one of a first Light Emitting Diode (LED) and a laser, wherein the first light source emits a first light of a first color, wherein the first color is a color other than green;
applying a second potential to a second light source comprising a linear array of LEDs to generate second light in a second color, wherein the second color is a color other than green, which second light is directed at a luminescent rod having a straight longitudinal surface parallel to said linear array of LEDs such that the luminescent rod is excited along a length of the luminescent rod such that the second light is absorbed by the luminescent rod which then generates by luminescence and emits green light through an outlet aperture of the luminescent rod; and
combining the first light and the green light into a combined beam on an optical axis and focusing said combined beam into a liquid light guide adapted to couple the combined beam into a fiber optic device.

12. The method of claim 11 further comprising:
applying a third potential to a third light source, wherein the third light source is selected from one of a Light Emitting Diode (LED) and a laser, wherein the third light source emits a third light of a third color different than the first color, wherein the third color is a color other than green; and
wherein said combining step includes combining said first light, said green light, and said third light into a combined beam on an optical axis and focusing said combined beam into a liquid light guide adapted to couple the combined beam into a fiber optic device.

13. The method of claim 12, wherein said combined beam comprises white light.

14. The method of claim 12, further comprising:
applying a fourth potential to a fourth light source, wherein the fourth light source is a Light Emitting Diode (LED), wherein the fourth light source emits a fourth light of a fourth color different than the first color and the third color, wherein the fourth color is a color other than green; and
wherein said combining step includes combining said first light, said green light, said third light, and said fourth light into a combined beam on an optical axis and focusing said combined beam into a liquid light guide adapted to couple the combined beam into a fiber optic device.

15. The method of claim 11, wherein said first light source includes a plurality of LED light sources that emit the first light of the first color.

16. The method of claim 11, wherein said combining step includes combining the first light and the green light into a combined beam on an optical axis using a combination of one or more collimators and dichroic mirrors and focusing said combined beam into a liquid light guide adapted to couple the combined beam into a fiber optic device.

17. The method of claim 11, further comprising cooling said luminescent rod by forcing air along said luminescent rod.

18. The method of claim 11, further comprising cooling said luminescent rod.

19. The fiber optic illumination system of claim 1, further comprising:
a laser light source which emits coherent light; and
wherein the associated optics combines the coherent light of the laser light source with the first light of the first light source and the green light generated by the luminescent rod into a combined light beam on the same optical axis and focuses said combined light beam into said liquid light guide.

20. The fiber optic illumination system of claim 1 further comprising:
a third LED light source which emits red light, and
a laser light source which emits coherent light;
wherein the first light emitted by the first LED light source is blue light; and
wherein the associated optics combines the red light of the third light source with the blue light of the first light source and the green light generated by the luminescent rod and the coherent light emitted by the laser light source into a combined light beam on the same optical axis and focuses said combined light beam into said liquid light guide.

21. An illuminator, comprising:
a first LED light source which emits a first light of a first color;
a luminescent rod light source, wherein the luminescent rod light source includes,
a linear array of blue LEDs which emits blue light,
a luminescent rod having a straight longitudinal surface parallel to said linear array of blue LEDs such that the luminescent rod receives the blue light from the linear array of blue LEDs, the luminescent rod made from a material which absorbs the blue light and generates green light by luminescence, wherein the green light is emitted through an outlet aperture of the luminescent rod;

one or more lenses and mirrors that combine the first light and the green light into a combined light beam and focus said combined light beam into a liquid light guide.

22. The illuminator of claim 21 further comprising:

a second LED light source which emits second light of a second color different than the first color;

a third LED light source which emits third light of a third color different than the first color and second color; and wherein the one or more lenses and mirrors combine the first light, the second light, the third light, and the green light into a combined light beam and focus said combined light beam into the liquid light guide.

23. The illuminator of claim 22, further comprising:

a fourth LED light source which emits a fourth light of a fourth color different than the first color, the second color, and the third color; and wherein the one or more lenses and mirrors combine the first light, the second light, the third light, the fourth light, and the green light into a combined light beam and focus said combined light beam into the liquid light guide.

24. The illuminator of claim 22, further comprising:

a laser light source which emits a coherent light; and wherein the one or more lenses and mirrors combine the first light, the second light, the third light, the coherent light, and the green light into a combined light beam and focus said combined light beam into the liquid light guide.

25. The illuminator of claim 22, wherein the combined light beam comprises white light.

26. The illuminator of claim 22, further comprising a high pressure fan adapted to cool the luminescent rod by directing air between the linear array of blue LEDs and the straight longitudinal surface of the luminescent rod.

27. The illuminator of claim 22, wherein the luminescent rod light source comprises a plurality of linear arrays of LEDs, the plurality of linear arrays positioned parallel to the luminescent rod with the LEDs no greater than 200 microns from the luminescent rod.

28. The illuminator of claim 22, wherein the luminescent rod comprises one of a single crystal Ce:YAG rod and a sintered ceramic Ce:YAG rod.

29. The illuminator of claim 22, wherein the first color is red.

30. The illuminator of claim 22, wherein liquid light guide is adapted to couple the illuminator to one of a microscope and an endoscope.

31. The illuminator of claim 22, further comprising a reflective element positioned at one end of the luminescent rod to reflect green light towards the outlet aperture.

* * * * *